(12) United States Patent
Brunner et al.

(10) Patent No.: US 6,257,265 B1
(45) Date of Patent: Jul. 10, 2001

(54) APPARATUS FOR CONNECTING A HEAT EXCHANGER WITH A FLUID TEMPERATURE REGULATION DEVICE

(75) Inventors: Charles Brunner, North Reading; Richard Plaisted, Cataumet; Peter MacDougall, Cambridge, all of MA (US)

(73) Assignee: Sims Level 1 Inc., Rockland, MA (US)

( * ) Notice: Subject to any disclaimer, the term of this patent is extended or adjusted under 35 U.S.C. 154(b) by 0 days.

(21) Appl. No.: 09/426,752

(22) Filed: Oct. 26, 1999

(51) Int. Cl.[7] .................................................. A61M 5/00
(52) U.S. Cl. ............................. 137/1; 137/340; 137/552; 137/557; 604/113; 604/118
(58) Field of Search ..................... 604/113, 118; 137/551, 552, 557, 340, 1; 251/149.5

(56) References Cited

U.S. PATENT DOCUMENTS

| | | | |
|---|---|---|---|
| 3,383,085 | * | 5/1968 | Vielmo ............................. 251/149.5 |
| 4,678,460 | * | 7/1987 | Rosner ................................ 604/113 |
| 4,759,749 | * | 7/1988 | Verkaart ............................. 604/113 |
| 4,874,359 | * | 10/1989 | White et al. . |
| 5,308,320 | * | 5/1994 | Safar et al. ............................... 604/4 |

* cited by examiner

Primary Examiner—A. Michael Chambers
(74) Attorney, Agent, or Firm—Louis Woo

(57) ABSTRACT

The temperature regulating device of the instant invention accurately regulates the temperature of a fluid to be sent through a conduit for either warming or cooling an infusate that is to be provided to a patient. The heater/cooler that is used for regulating the temperature of the fluid, and the fluid itself, are continuously monitored by a number of sensors, which provide feedback signals to a processor controller, to ensure that the temperature of the fluid is maintained at a desired temperature. The fluid is circulated by a pump which operation is also continuously monitored. A special connector assembly provides the inlet/outlet connection between the device and the fluid conduit. The connector assembly is constructed such that the system would operate only when the connector of the fluid conduit is correctly mated thereto. A calibration device, shaped substantially the same as the connector for the fluid conduit, when mated to the connector assembly, initiates a sequence that include the calibration and testing of various temperature sensitive components in the device.

21 Claims, 16 Drawing Sheets

TURNING UNIT OFF

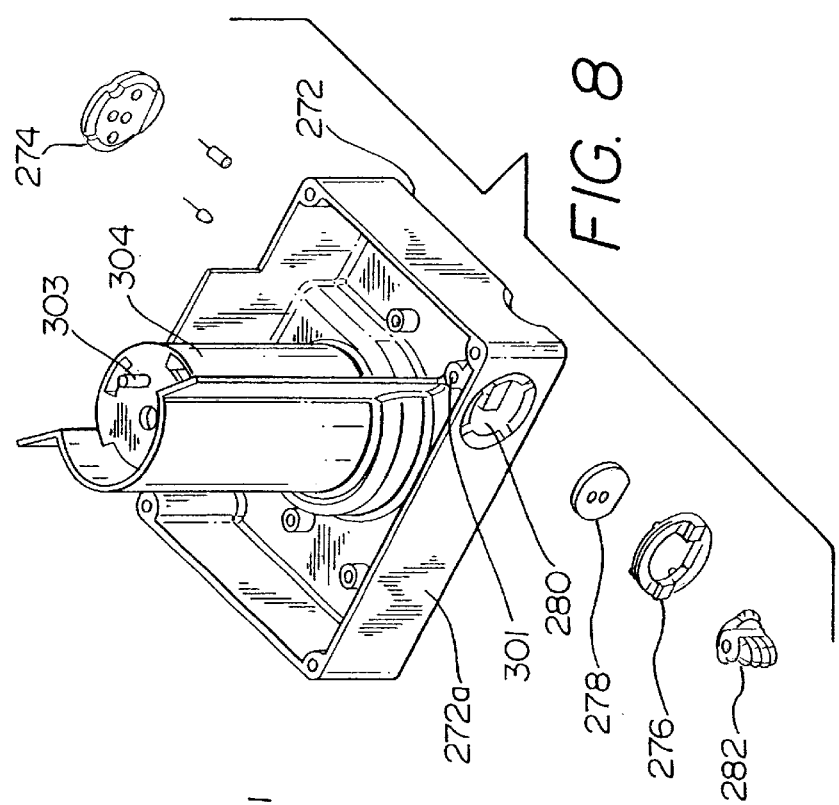
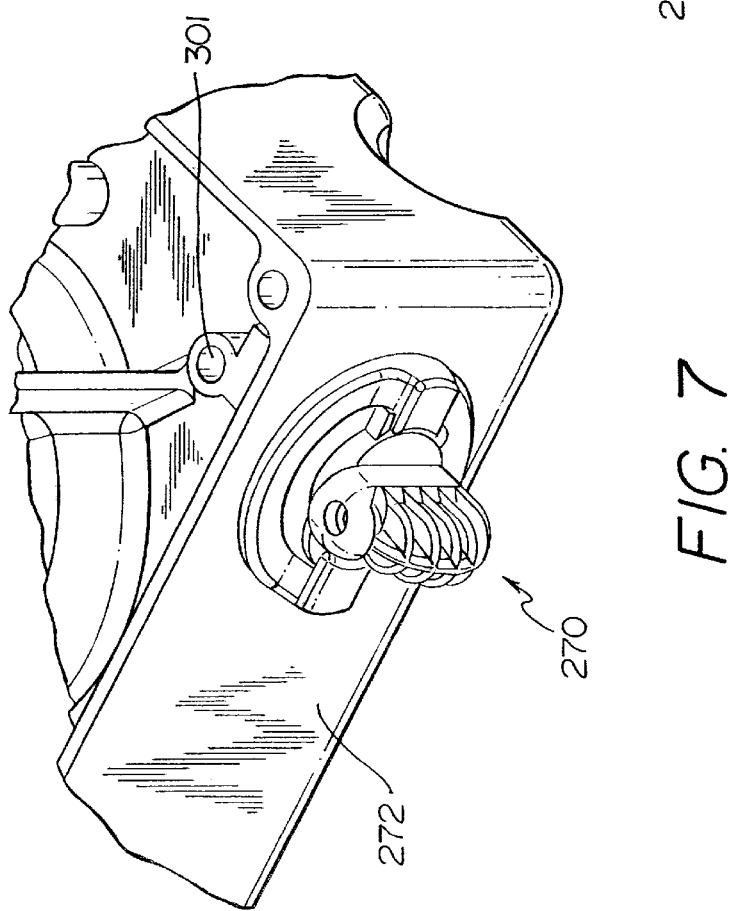

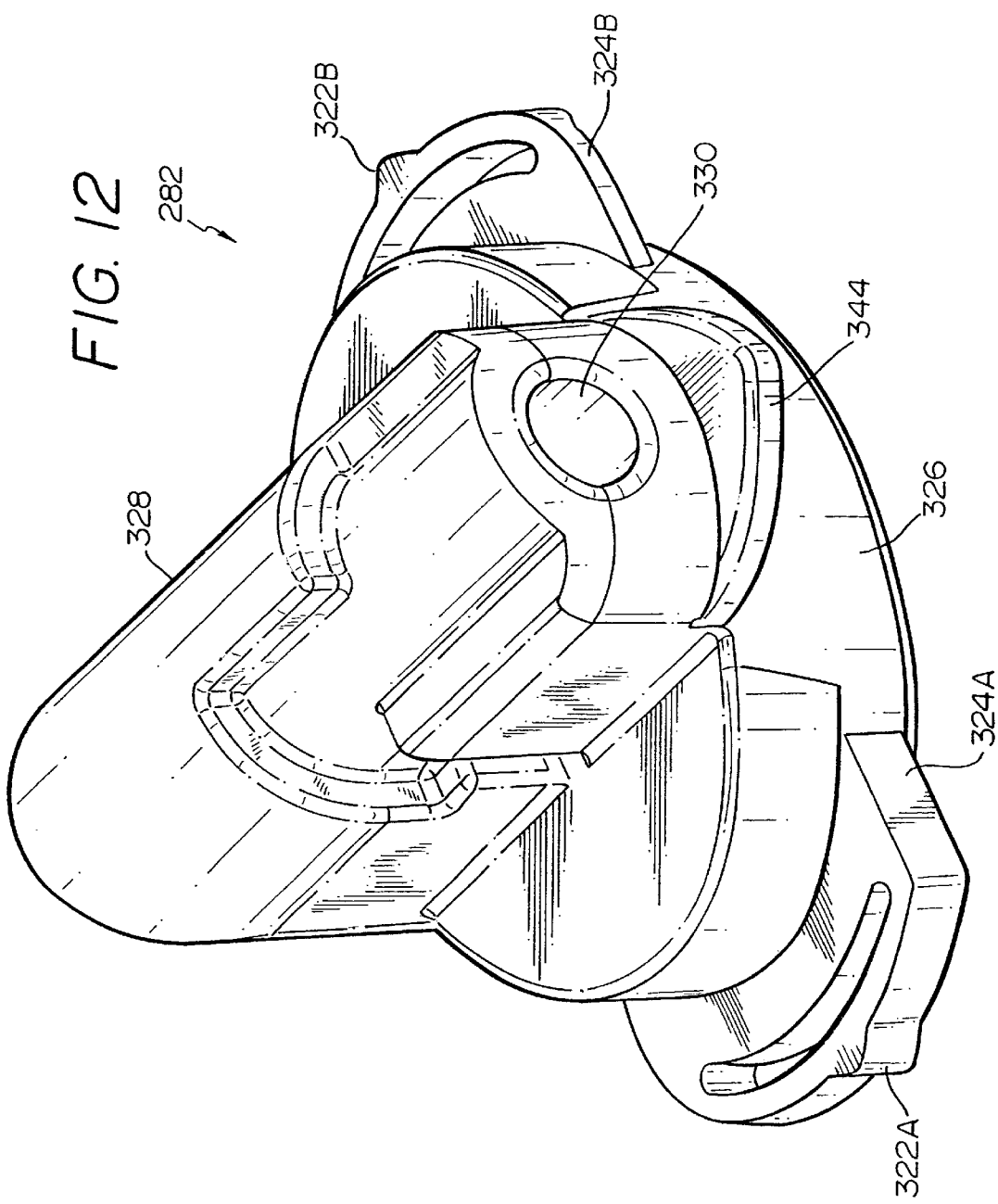

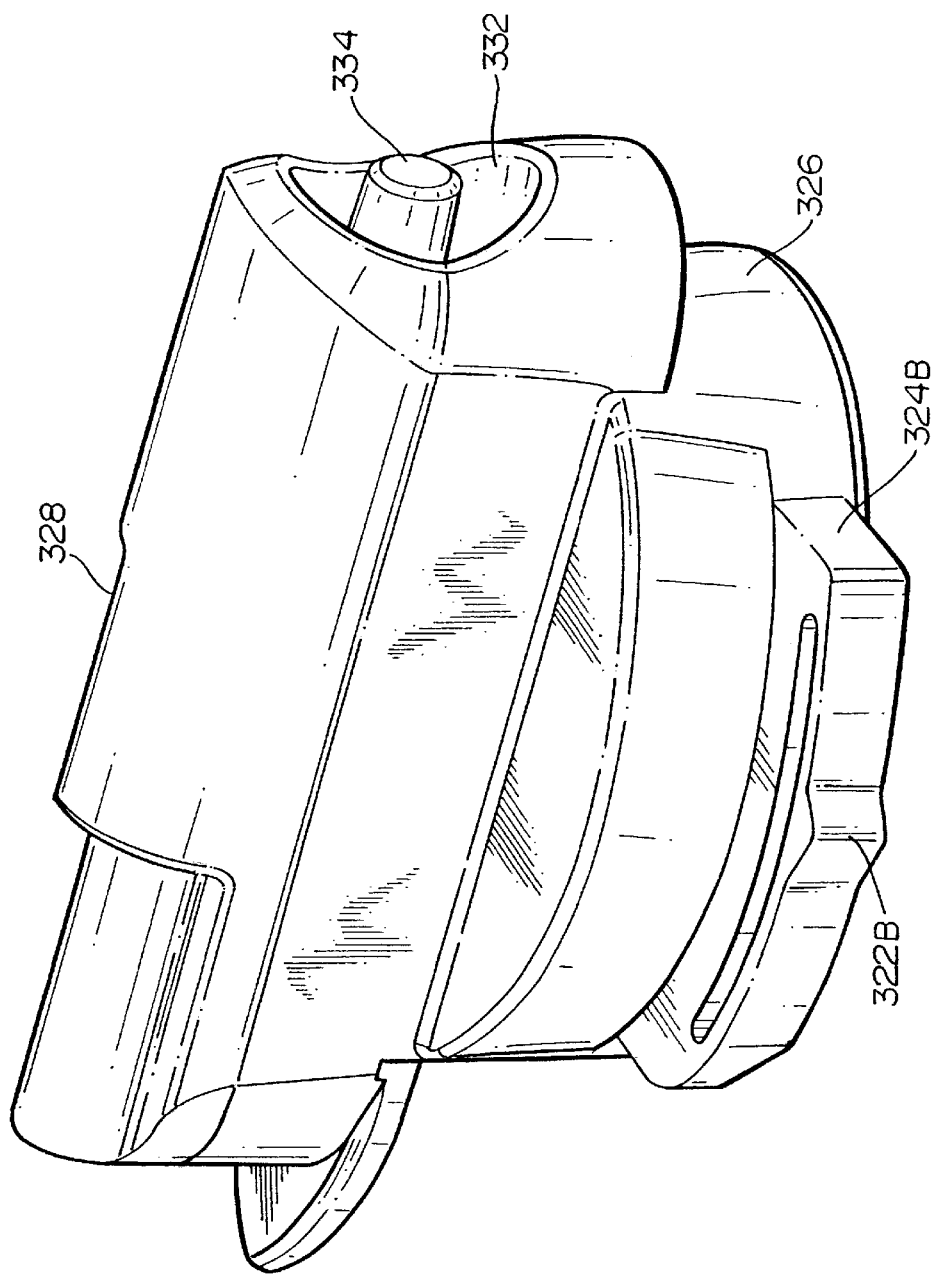

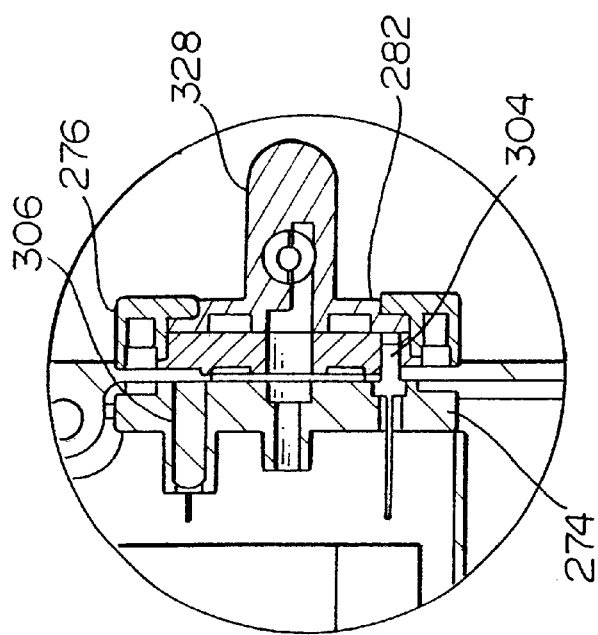
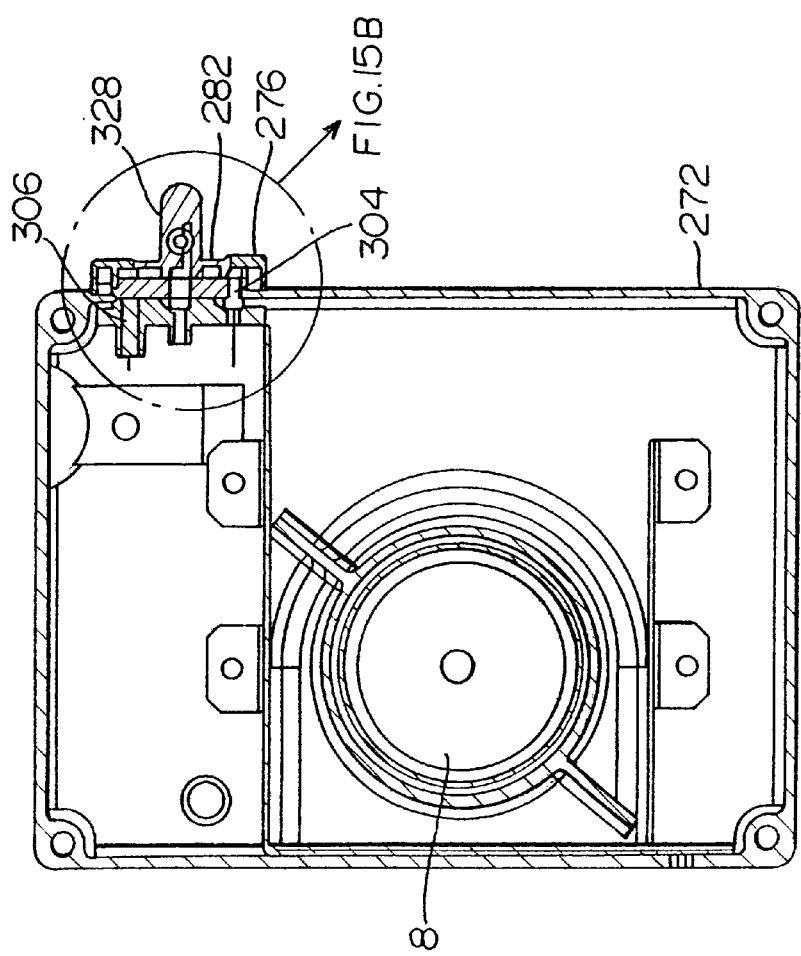

APPARATUS FOR CONNECTING A HEAT EXCHANGER WITH A FLUID TEMPERATURE REGULATION DEVICE

FIELD OF THE INVENTION

The present invention relates to temperature regulating devices, and particularly a temperature regulating device for physiological fluids and a connector assembly integrated thereto for interconnecting a fluid conduit to the device so that a fluid of a desired temperature can be provided via the fluid conduit to a patient.

BACKGROUND OF THE INVENTION

Devices for warming physiological fluids, such as for example whole blood and packed cells, to a desired temperature before providing the warmed physiological fluids to a patient are well known. Once such prior art device is the HOTLINE® system made by the assignee of the instant invention. Such a device uses a heater and hardwired control for heating a fluid such as for example water to a desire temperature, so that the water can in turn warm the infusate to be provided to the patient via a fluid conduit. Inasmuch as the feedback for such system is hardwired, its feedback response is somewhat limited. Moreover, given the limitation of the display mechanism in the prior art HOTLINE® device, no meaningful interfacing between the device and the user is achieved.

So, too, given that the first generation HOTLINE® device is hardwired, in order to determine the integrity of its temperature sensing components, a technician has to physically open up the device, and then test each one of the individual components. This need for disassembling the machine in order to test the integrity of its sensors and other components, needless to say, is time consuming and expensive. Furthermore, the hardwired control circuit for the prior art device does not provide the flexibility or capacity to enable the adding or modification of data that a clinician may want, but which had not been hardwired into the system.

SUMMARY OF THE PRESENT INVENTION

The device of the instant invention for regulating the temperature of a fluid is divided into three main sections, namely a controller section, a temperature regulator section and a user interface section. In the temperature regulation section, there is a reservoir wherein in a fluid that is to be temperature regulated is stored. Such fluid may be for example water. The fluid is driven by a pump to a heater, or cooler, so that the temperature of the fluid may be warmed or cooled to a desired temperature. The regulated temperature of the fluid is then sensed by thermistors, which provide a feedback to a processor at the controller section. The sensed temperature is compared with a preset temperature for maintaining the temperature of the fluid to the desired temperature.

The thus temperature regulated fluid is provided to bidirectional ports, which are coupled to a connector assembly that effects an interface between the device and a disposable fluid conduit. The temperature regulated fluid warms/cools an infusate that is also being carried along the fluid conduit and provided to a patient. A couple of sensors or switches are located proximate to the connector assembly for ensuring that the fluid conduit is positively connected to the connector assembly and that there has not been any tampering with the connector assembly. In the case that tampering is detected, a signal may be provided to the processor to shut down the system, so that the device could not work without the user having to first return it to the factory for repair. Such repair may require the replacement of a ROM chip which algorithm is either destroyed or erased when the sensor senses that the connector assembly has been tampered with.

The connector assembly is designed in such a way that the circulation of the fluid conduit occurs only if the fluid conduit is correctly mated to the connector assembly. To test the integrity of the temperature regulating section, the fluid conduit can be replaced by a temperature calibration or checking device, Once the temperature checking device correctly fits to the connector assembly, a test takes place for determining the calibration and integrity of the various temperature sensing components in the temperature regulating section, to therefore ensure that the device is operating properly.

The controller section of the device of the instant invention has as its main component the controller processor, which may be a conventional microprocessor. There are a number of functions performed by the processor. These include monitoring the current being used by the pump motor by means of a current sensor. The thus sensed motor current of the pump is then used by the processor as a feedback to determine the load being placed on the pump and whether the pump is operating within an acceptable range. The temperature of the temperature regulated fluid is continuously monitored by a pair of thermistors, and fed back to the processor, which then uses the feedback temperature to determine if the operation of the device should continue. This is done by the processor determining whether there is a difference between the respective temperatures sensed by the thermistors and/or whether either one of the thermistors has sensed an overheated temperature for the fluid.

The processor further monitors the sensors that are positioned proximate to the connector assembly so as to continuously monitor whether the fluid conduit is correctly mounted to the connector assembly and whether a temperature calibration device has been fitted to the connector assembly in place of the fluid conduit. If a temperature calibration device is sensed, calibration and testing of the functionality of the thermistors and a fail-safe thermostat would take place. As was discussed before, any tampering with the connector assembly may be sensed by the processor, which then could output an instruction to inhibit, destroy or erase an algorithm in a particular memory store such as for example a ROM so as to shut down the system.

The controller also interacts with the user interface section. There, a display, preferably in the form of a LCD display, is provided so that instructions in any one of a plurality of languages stored in the controller section of the device can be displayed to the user. To operate the machine, either a touch sensitive screen or input keys placed on the front of the user interface section are used. Different lights at the user interface section provide the user with a constant indication of the operational status of the device of the instant invention.

Insofar as the temperature regulation device of the instant invention is processor controlled, the various functions that the device performs can therefore be controlled by software, as compared to the prior art devices which require hardwired operations. Accordingly, the functions of the device of the instant invention are readily changeable, checked and controlled.

It is therefore an objective of the present invention to provide a device that regulates the temperature of a fluid by continuous feedback.

It is another objective of the device of the instant invention to have the ability for self testing the integrity of its various components in its temperature regulation section on each power on.

It is yet another objective of the present invention to provide an interface that is adaptable to be used by people using different languages.

It is still yet another objective of the present invention to provide a temperature regulating device that has functions that are readily upgradable, without any need to disassemble the device.

BRIEF DESCRIPTION OF THE FIGURES

The above-mentioned objectives and advantages of the present invention will become apparent and the invention itself will be best understood by reference to the following description of an embodiment of the invention taken in conjunction with the accompanying drawings, wherein:

FIG. 7 is a perspective view of the connector assembly of the instant invention, as it is incorporated into the housing of the device of the instant invention;

FIG. 8 is a perspective exposed view of the various components of the connector assembly of the instant invention;

FIG. 10b is a perspective bottom view of the support plate of the connector assembly of FIG. 10a;

FIG. 12 is a perspective semi-exposed view of the connector body of the connector assembly of the instant invention to which is connected a fluid conduit through which the infusate to be provided to the patient flows;

FIG. 13 is another perspective view of the connector body of the FIG. 12;

FIG. 15a is a plan view of the housing of the device of the instant invention with the connector assembly being integrated thereto;

FIG. 15b is an enlarged view of the connector assembly and the mating thereto of the connector of FIG. 12;

DETAILED DESCRIPTION OF THE INVENTION

Figure 1:
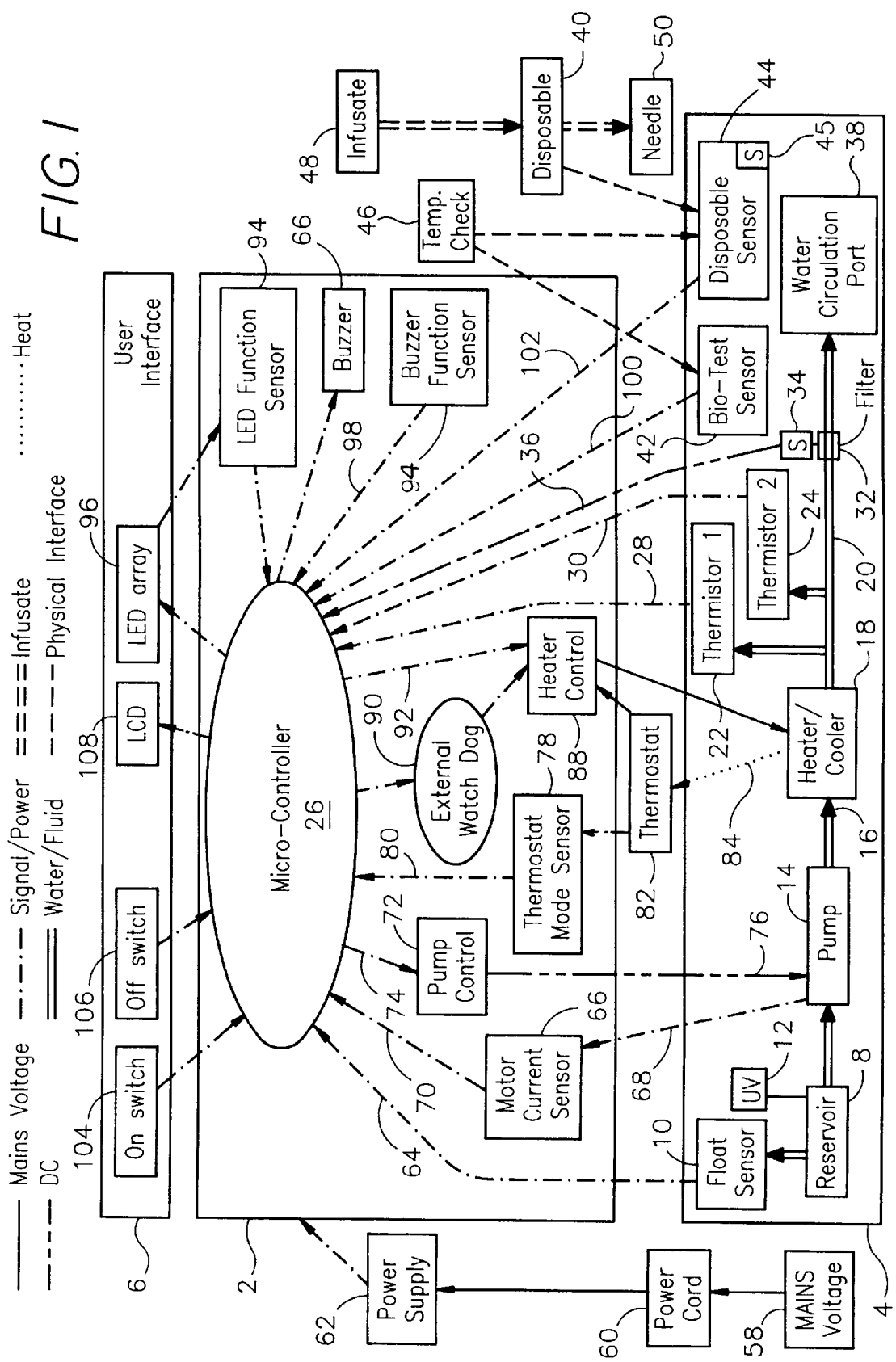
FIG. 1 is a block diagram illustrating the various components of the device of the instant invention.

With reference to FIG. 1, the temperature regulating device of the instant invention is shown to include three major sections—a controller section 2, a temperature regulation section 4 and a user interface section 6. The three sections are communicatively interconnected.

As shown, temperature regulation section 4 has a reservoir 8 for storing the fluid that is to be temperature regulated. The fluid could be any type of fluid including non-compressible fluid or gas. But for the discussion of the exemplar embodiment, water is the preferred fluid to be used. Reservoir 8 has communicatively connected thereto a float sensor 10 that senses the level of fluid in reservoir 8. There may also be positioned relative to reservoir 8 an ultraviolet light source 12 which could direct an ultraviolet light to the fluid in the reservoir for killing any bacteria and/or microbes that may find their way into the fluid stored in reservoir 8. Note that ultraviolet sensor 12 may also be positioned along the tubings that connect to the bidirectional inlet/outlet ports in the temperature regulation section 4 for killing any bacteria and/or microbes that may be in the tubings and/or in the fluid that flows through the tubings.

Reservoir 8 is connected to a pump 14, which is a bidirectional pump or equivalents thereof that may be purchased from a number of companies including the Gorman-Rupp Company. In essence, pump 14 could be a bidirectional positive displacement gear pump that can circulate the fluid in either a forward direction, as indicated for example by arrow 16, or in a reverse direction so as to route the fluid back into reservoir 8.

Pump 14 is connected to a heater, or cooler, 18 which, in the instance that it is operating as a heater, warms the fluid circulated thereto by pump 14 to a desired temperature. Alternatively, the fluid output from pump 14 may also be cooled by cooler 18 to a desired temperature. For ease of understanding, assume for the rest of this discussion, heater, or cooler, 18 works as a heater for warming a fluid output from pump 14.

The fluid, in this instance water, output from heater 18 is routed to a tubing 20 that has communicatively connected thereto two thermistors 22 and 24. These thermistors each independently sense the temperature of the fluid being heated by heater 18 and flowing along tubing 20. Respective signals are output by the thermistors to processor 26 via signal or channel lines 28 and 30. Thermistors 22 and 24 are each calibrated to a set point, so that theoretically each of the thermistors should measure the same temperature from the fluid flowing along tubing 20. If for any reason the respective temperatures measured by thermistors 22 and 24 diverge for more than a predetermined amount, such as for example 3° C., then processor 26, upon sensing this variance, would shut the system down. This is done in order to ensure that the temperature of the fluid being heated by heater 18 remains accurate.

Thermistors 22 and 24 each also work cooperatively with processor 26 to ensure that the system does not reach an overheated or overtemp condition. This is done by thermistors 22 and 24 each continuously reporting to processor 26 whether a temperature higher than the normal operating temperature, i.e., an "overtemp" condition such as for example 2° C. above the normal temperature, has been sensed. If either one of thermistors 22 and 24 senses such overtemp condition, the heater is shut down.

Alternatively, each of thermistors 22 and 24 is set to have its circuit electrically respond to the overtemp condition so as to automatically shut down the operation of heater 18. Once the system has been shut down due to an overtemp condition, the machine would remain in such fail-safe shut down mode.

To maintain the desired temperature of the fluid, one of thermistors 22 and 24 is used to activate a control relay to turn heater 18 "on" and "off" in response to the temperature of the fluid to thereby maintain the temperature of the heated fluid to be within an acceptable temperature range.

Further along tubing 20 there may be positioned a filter 32 that could filter out any bacteria and/or microbes that might be in the fluid. Filter 32 may have connected thereto a sensor 34, which may continuously monitor the filtering element of filter 32 for ensuring that the filter element continues to be able to filter out microbes and bacteria. Sensor 32 may do this by detecting the opacity of the filter element in filter 32. A signal from sensor 34 is fed to processor 26 by means of a signal line 36.

The fluid from tubing 20 is routed to a water circulation port 38 that comprises inlet/outlet bidirectional ports that enable the fluid from tubing 20 to be routed to a fluid conduit in the form of a disposable 40. Disposable 40 may be a triple lumen conduit such as that described in U.S. Pat. Nos. 5,097,898 and 5,063,994, the disclosures of which being incorporated by reference herein. Although not shown in FIG. 1, the mating of disposable 40 to bidirectional ports 38 is done by means of a connector assembly such as for example that shown in FIGS. 7–15. A more detailed discussion of the connector assembly and the connector mated thereto from which disposable 40 extends will be given, infra.

Return to FIG. 1. Note that there are a Bio-Test sensor 42 and a disposable sensor 44 each positioned relative to the bidirectional ports and the connector assembly as mentioned above. Sensor 42 and 44 will be discussed in detail with the discussion of the connector assembly. For now it suffices to say that Bio-Test sensor 42 is an electromagnetic sensor that senses the mating to the connector assembly of a calibration device such as a Temp Check 46 for initiating a test that determines the integrity of various components in temperature regulating section 4. Disposable sensor 44, on the other hand, is an electromechanical switch or sensor that continuously monitors whether the fluid conduit, i.e., disposable 40, or Temp Check 46 is fitted correctly to the connector assembly. If either, of disposable 40 or Temp Check 46 is not mated to the connector assembly properly, sensor 42 sends a signal to processor 26, which in turn prevents the instant invention device from working.

Moreover, an additional sensor 45, which may be either an electromagnetic sensor or an electromechanical switch positioned relative to the connector assembly, continuously monitors the integrity of the connector assembly. In the event that tampering of the connector assembly, such as for example the removal thereof, is detected, sensor 45 would send a signal to processor 26 to inform processor 26 to disable the device. This could be done by processor 26 sending a signal such as for example a delete signal to an EPROM, wherein various functional algorithms relating to the operation of the device are stored, to erase at least one of the algorithms that operates the device. Thereafter, to reenable the device, the device has to be returned to the factory so that the erased algorithm could be reinstored.

With respect to disposable 40, note that it includes the conduit to which infusate 48 is input so that the infusate can be provided to a needle 50, which is used to infuse the patient. Infusate 48, as it flows through disposable 40, is warmed to the desired temperature by the fluid that is being circulated from pump 14 to disposable 40.

Controller section 2 of the instant invention device has connected to its processor 26 a number of components. For example, a signal is provided to processor 26 from float sensor 10 via line 64. As mentioned previously, float sensor 10 senses the level of fluid in reservoir 8, so that if the level happens to fall below a predetermined level, processor 26 can notify the user that additional fluid is required via some indicator such as for example a buzzer 66 and/or a light at LED array 96. Moreover, if float sensor 18 were to sense the level of fluid in reservoir to be below a minimum level, it will send a signal to processor 26, which will then shut the system down.

Processor 26 has also input thereto a signal from a motor current sensor 66 that senses the current of pump 14 by way of a signal line 68 to pump 14. The value of the sensed current informs processor 26 of the operational status of pump 14. To wit, if sensor 66 senses a normal current, for example from 100–500 $\mu$A, then processor 26 knows that pump 14 is operating normally. However, if the current is sensed to be above 500 $\mu$A, for example between 500 and 800 $\mu$A, then processor 26 knows that something is wrong. Accordingly, a "NOT WARMING" warning is displayed to the user. At this stage, the problem could be one that is readily fixable, such as for example disposable 40 having a kink that is easily straightened out. Finally, if the sensed current from pump 14 has a value greater than a predetermined amount, for example 800 $\mu$A, then processor 26 knows that something is wrong with the motor of pump 14. At this time, in addition to displaying the "NOT WARMING" warning, processor 26 could also shut down pump 14 to prevent any potential damage thereto.

Processor 26 is further connected to a pump control 72 by means of a signal line 74. Pump control 72 controls the direction of rotation of pump 14 for circulation of the fluid in either the forward direction, as exemplified by arrow 16, or the reverse direction so as to drain the fluid in disposable 40 and tubing 20 back into reservoir 8. In receipt of a turn off signal, processor 26 would instruct pump control 72 to reverse the rotation of pump 14 to thereby drain the fluid in tubing 20 and disposable 40 back into reservoir 8.

A thermostat mode sensor 78 is communicatively connected to processor 26 via a signal line 80. Thermostat mode sensor 78 is also connected to an external thermostat 82, which continuously monitors the operating temperature of heater 18 via a signal line 84. Thermostat 82 is a "fail-sale" device in that it is preset to a given temperature that, if sensed, causes it to shut down the system so as to prevent any catastrophic damage to the device and potential harm to the patient. Thermostat 82 therefore acts as a backup to thermistors 22 and 24 in the event that both of those thermistors fail. Thus, the shut down temperature in thermostat 82 is preset to a value that is higher than the set point temperature and the overtemp condition thermistors 22 and 24 each were calibrated to respond to, and quite a bit higher than what is considered to be the operating temperature of heater 18.

In the meantime, whether thermostat 82 is operating properly is periodically being monitored by thermostat mode sensor 78. Sensor 78 could be an inductor coil placed about the conductor that provides power to thermostat 82 so as to sense the current flowing through thermostat 82. If per chance thermostat 82 fails, sensor 78 can sense that there is no current flowing therethrough. It will accordingly inform processor 26 that thermostat 82 has malfunctioned.

An external watchdog module 90, which is an electrical circuit that comprises a Schmidt trigger and its own time base, is communicatively connected to processor 26. Watchdog 90 continuously monitors the operation of processor 26 per its timing and compares the time base of processor 26 with its own clock pulses to ensure that processor 26 is operating properly. Watchdog 90 would shut the system down if it senses that processor 26 is not functioning properly by cutting off power to heater 18, such as for example by opening a safety relay that connects heater 18 to its power source. Note that in addition to external watchdog 90, there is an internal watchdog in controller 26 that monitors the execution of the software of the system.

Other components connected to processor 26 that reside on section 2 include an LED function sensor 94 that senses the operation of LED array 96 located in user interface section 6. Buzzer 66, as mentioned previously, may be used to alert the user of problems in the device of the instant invention that he or she should be made aware of. In particular, buzzer 66 outputs different sound signals for different problems, as for example three beeps or a specific tone for an "OVERTEMP" condition as compared to one beep or another tone for a "NOT WARMING" condition. A buzzer function sensor 96 senses the signals output from buzzer 66 and provides a feedback to processor 26 by means of a feedback signal line 98.

Processor 26 is further communicatively connected to Bio-Test sensor 42 and disposable sensor 44 by means of signal lines 100 and 102, respectively. When a signal is sent by Bio-Test sensor 42 to processor 26 to inform it that Temp Check 46 is in place, processor 26 begins a calibration and temperature testing procedure for determining the integrity of various components of the system. These components include thermistors 22, 24 and thermostat 82.

In particular, each of thermistors 22 and 24 is calibrated to respond to a given set point, for example 41.9° C., that the temperature of the fluid is to be regulated at. Moreover, thermistors 22 and 24 each are tested to ensure that they each will electrically respond to an "overtemp" condition. An overtemp condition may for example be set to occur if the temperature of the fluid is measured to be 1.5° C. above the set point. When either of thermistors 22 and 24 senses the "overtemp" condition, heater 18 is shut down.

Thermostat 82 is tested separably from both thermistors 22 and 24. Bypassing thermistors 22 and 24, thermostat 82 is tested to determine if it will open at a predetermined fail-safe-temperature that is well above the temperature at which thermistors 22 and 24 each become electrically open. In other words, by making sure that thermostat 82 will open at the failsafe temperature, the system is ensured to shut down at that predetermined fail-safe temperature to prevent any catastrophic occurrences.

The last major section in the device of the instant invention is user interface section 6. As shown, user interface section 6 has an on switch 104, an off switch 106, a LCD display 108, as well as the previously mentioned LED array 96. The on and off switches 104, 106 are switches that, once activated, would signal processor 26 to take different predetermined courses of action, which will be discussed in detail with respect to the flow diagrams of FIGS. 2 and 6. LCD display 108 is a display that provides to the user messages in any one of a plurality of languages so that the device of the instant invention can be shipped to various countries without having to have its menus and instructions reprogrammed specifically for the country that it is to be shipped to. The interaction between LCD display 108 and controller 28 is conventional in that the typical drivers and signal generators, as well as conventional memory stores such as ROMs that store the different languages and menus, are used. LED array 96, as was discussed previously, provides the user an indication of the types of functions that the device is performing. A touch sensitive screen or input keys provide the interfacing between the user and the instant invention device.

Figure 2:
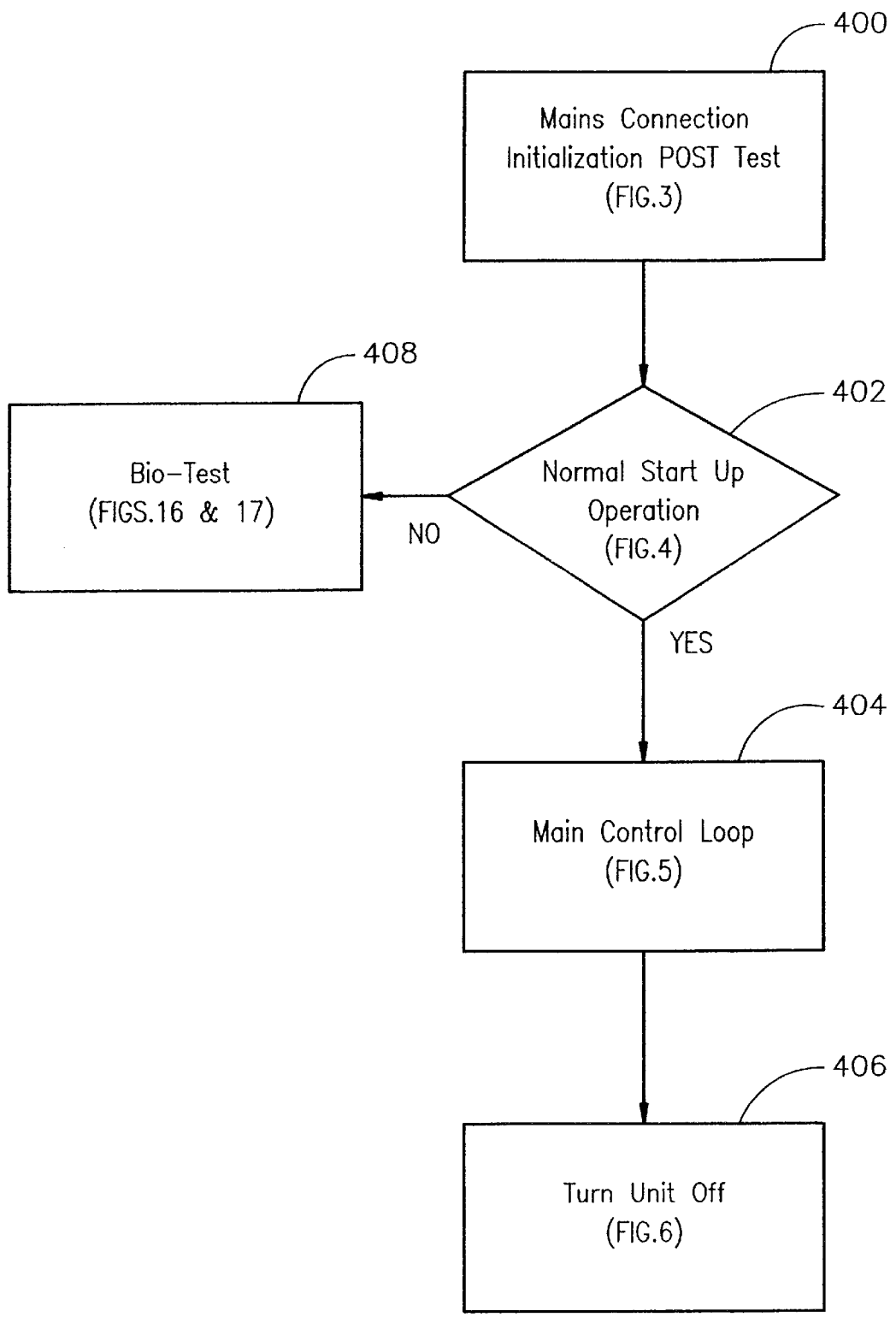
FIG. 2 is a flow diagram providing an overall view of the various functions of the device of the instant invention.

An overall top level flow diagram illustrating the main operation processes of the system of the instant invention is shown in FIG. 2 As shown, there are five major processes. These are: Mains Connection, Initialization and Power On Testing process 400; Normal Operation Process 402; Main Control process 404; Turn Off process 406 and Bio-test process 408. These processes are to be discussed hereinbelow with reference to FIGS. 3–6.

Figure 3:
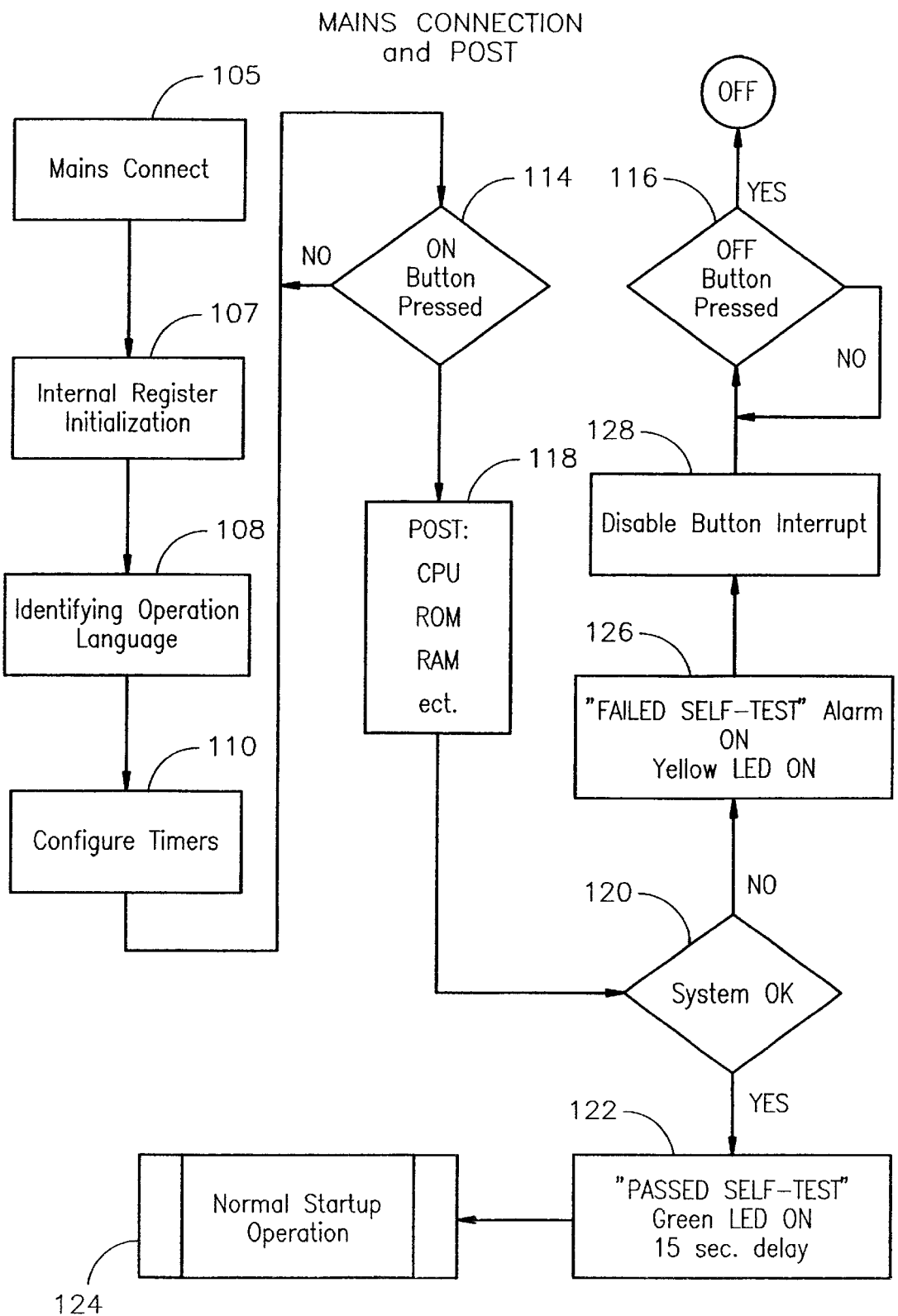
FIG. 3 is a flow diagram illustrating the Power On and Self Test procedures of the instant invention device.

With reference to FIG. 3, a combination Mains Connection and Power On Self Test (POST) flow chart is provided. The Power On process begins when the mains are connected at step 105. The POST process is initiated at step 114 when ON switch 104 is pressed. Briefly, the power on test is a self test to be performed by the system to test its various components such as for example its RAM, ROM and any other component that may deal with the safety or temperature regulating aspect of the device. As its name implies, every time that the machine is turned on, the testing of the various components of the system is performed.

In particular, starting at step 105, mains are connected. Thereafter, an initialization test 107 is performed in the read only memory (ROM) of the device in which the various programs or software routines for performing the various functions of the device is tested. A test is also performed on the random access memory (RAM) of the device. The internal register of the device is also initialized. Such internal register initialization also includes the initialization of the LCD display and the EEPROM. Note that such ROM, RAM, EEPROM and registers are common in electronic devices and therefore not shown in the block diagram of the device as illustrated in FIG. 1.

Following the initialization in step 107, the process proceeds to step 108 in which the operation language is identified. This operation language could be any one of a plurality of languages stored in a memory in the device so that the device can be sold in most of the countries of the world.

In step 110, the timers are initialized. Internal watchdog operation begins to monitor program flow. Note that steps 107–110 do not need to be processed in the particular order shown.

Next, the process waits until on button 104 is pushed, per step 114. When the on button is pushed, the system proceeds to step 118 to perform the POST test for determining the integrity of the various components of the system. This POST process includes testing of all components associated with the safety of the system such as the CPU, RAM, ROM, etc. If the system tests out okay per step 120, the appropriate green LED at LED array 96 is lit, per step 122, to indicate to the user that the system is operational. Thereafter, per step 124, the device proceeds to perform the normal operation, and the POST process is completed.

However, if the system tests abnormal in step 120, a failed self test alarm, as indicated by a yellow LED in LED array 96, is lit to indicate to the user that the self test has failed. If there is a failed self test, the process proceeds to step 128 to output a disabled interrupt to the processor for disabling the system. The process then waits until the off button is pressed by the user per step 116 to turn off the system.

Figure 4:
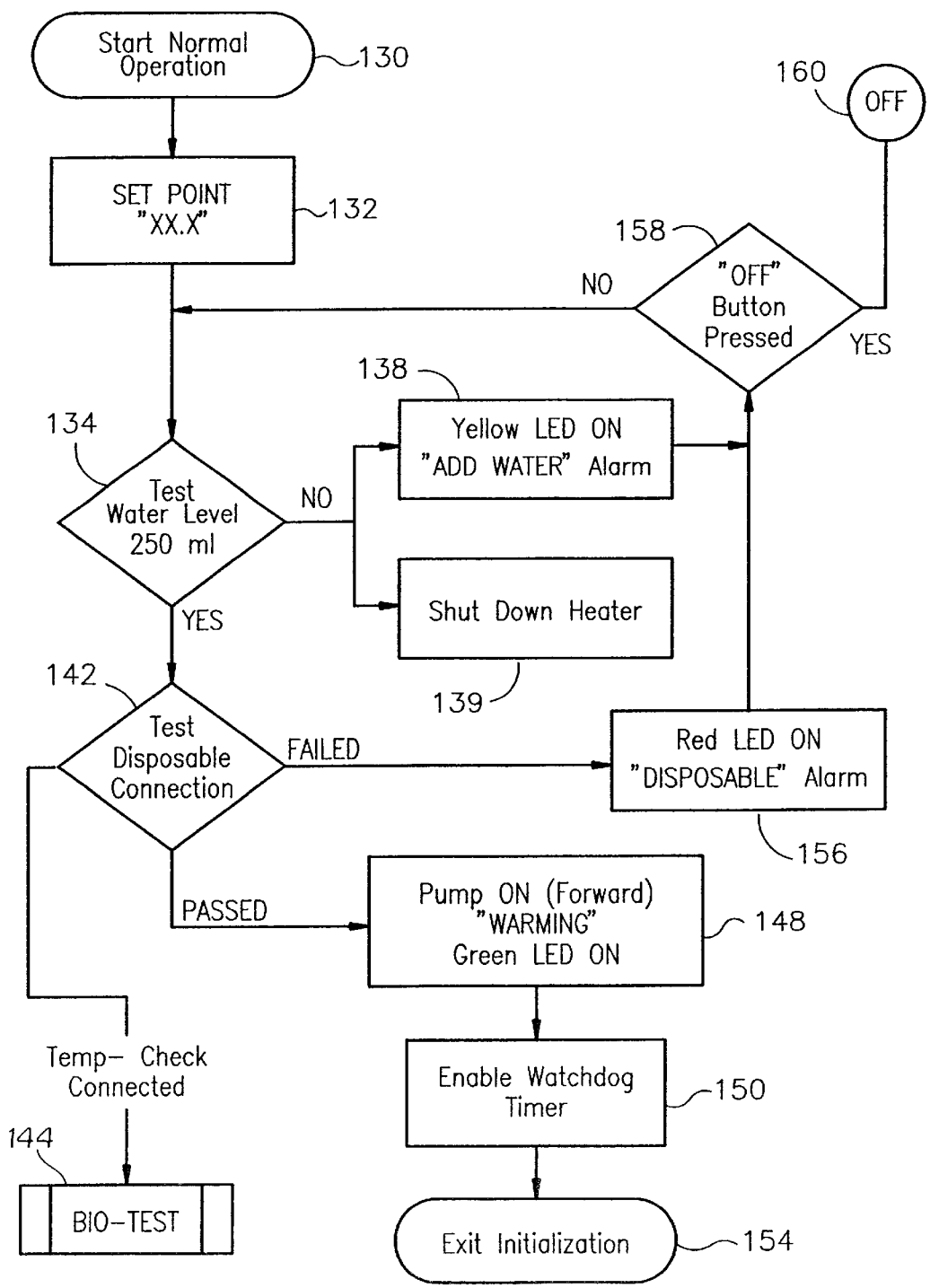
FIG. 4 is a flow chart illustrating the Normal Operation and Initialization processes of the instant invention device.

The Normal Start Up Operation process is illustrated in FIG. 4, A predetermined set point temperature is provided by the user and read at step 132. At step 134, the fluid level is tested to determine whether it is at least 250 ml, the minimum fluid level allowing the machine to operate. Any level lower, the machine will shut down. If the fluid level is sensed to be between 250 ml and 300 ml, fluid needs to be added to reservoir 8. Thus, if per step 134, the water level is determined to be less than 250 ml, a yellow LED is lit on LED array 96 to indicate to the user that he or she should add fluid, per step 138. At the same time, power is shut off for heater 18 per step 139. The device, in the meantime, will not operate. On the other hand, if the level of fluid is above 250 ml but below 300 ml, the yellow LED is lit on LED array 96 to indicate to the user that the fluid level in reservoir 8 is low, and the message "Water Tank Low" is flashed periodically on the LCD display.

Figure 16:
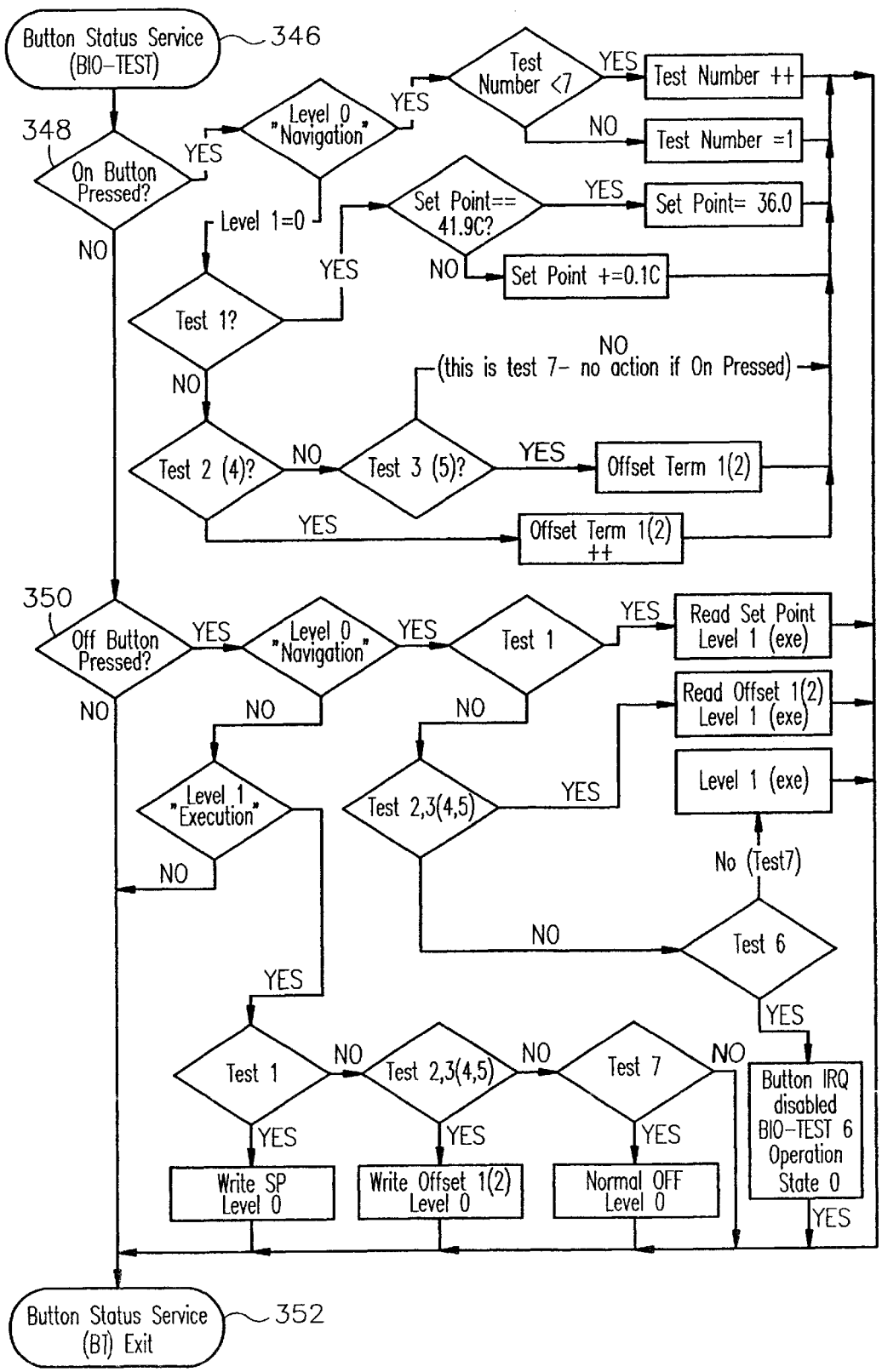
FIG. 16 is a flow diagram illustrating the self-testing procedure of the instant invention.

The next step of the normal start up operation process is step 142, which tests whether the disposable fluid conduit has been properly connected to the connector assembly. If it turns out that Temp Check 46 is properly fitted to the connector assembly, the "Bio-Test" of the system, which is shown in much greater detail in FIGS. 16 and 17, begins, per step 144.

On the other hand, if a fluid conduit is determined to have been properly connected to the connector assembly per step 142, the process proceeds to step 148 to initialize pump 14 to circulate the temperature regulated fluid, and light the green LED on LED array 96 to indicate to the user that the device is operating normally. Thereafter, the timer for external watchdog 90 is enabled, per step 150. After which the operation process exits from its start up phase, per step 154.

Return to step 142 where a determination is made on whether the connector for the fluid conduit has been properly connected to the connector assembly. If it is determined that the fluid conduit connector is not properly connected, a yellow LED relating to disposable fluid conduit 40 is lit on LED array 96 to indicate to the user that disposable 40 is not properly connected, per step 156. Thereafter, the process waits for the activation of the off switch, per step 158. Once the off button is pressed per step 158, the device is turned off, per step 160.

Figure 5:
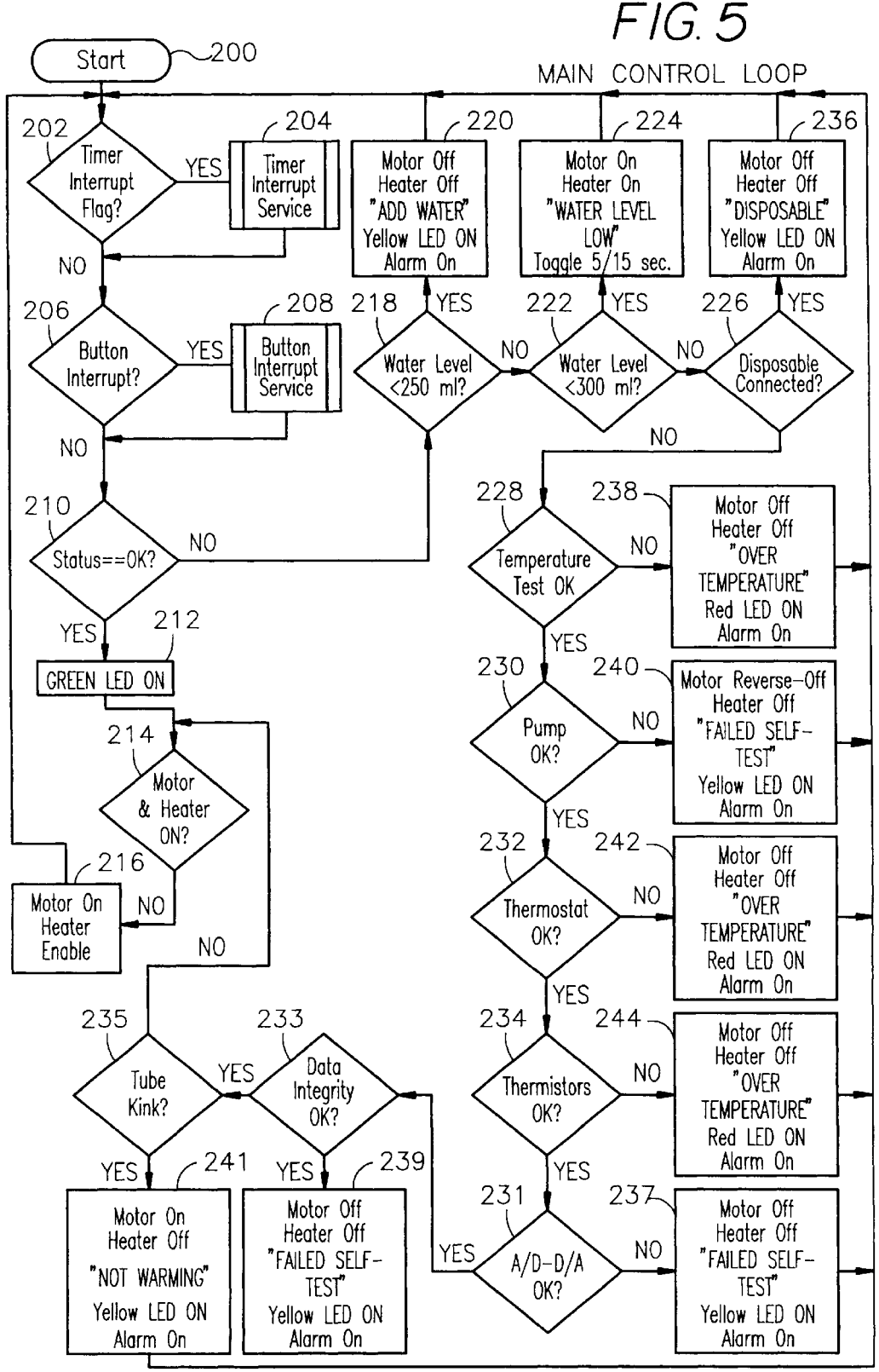
FIG. 5 is a flow chart that illustrates the Main Control Loop process of the instant invention.

After the normal start up process as illustrated in the flow chart of FIG. 4, the operation of the device proceeds to the Main Control Loop process as illustrated in the flow chart of FIG. 5. From the start step 200, the process proceeds to step 202 for determining whether the timer interrupt flag has been raised. If it has, the process proceeds to timer interrupt service per step 204 for clearing the timer interrupt. If there is no timer interrupt, the process proceeds to step 206 to determine whether any buttons have been pushed. If a button has been pushed, the process proceeds to step 208 for the user to do what he or she needs to do to clear the button interrupt. The process then proceeds to step 210 at which time the system determines whether its overall status is okay. If it is, the green LED at LED array 96 is lit, per step 212 to signify that the system is operational.

Thereafter, a determination is made on whether pump 14 and heater 18 each have been turned on, per step 214. If yes, the process proceeds back to the beginning of the loop process to wait for an interrupt from either the timer or the off switch, per steps 202 and 204, respectively. If on the other hand, per step 214, it is determined that pump 14 and heater 18 have not been turned on, the process proceeds to step 216 to turn on pump 14 and heater 18. The process then proceeds to the beginning of the loop to wait for either the timer interrupt or the button interrupt, as indicated per steps 202 or 206, respectively.

As mentioned previously, provided that the status of the device remains okay at step 210, the device is deemed to be operational and the green LED is lit per step 212. However, if it is determined per step 210 that any one of the tests as shown in FIG. 5 has failed, then a number of additional tests will take place. This is illustrated starting with step 218 in which a determination is made on whether the fluid level is less than the minimum acceptable level. If it is less than the minimal acceptable level, pump 14 and heater 18 are each turned off, per step 220. Also, per step 220, the "add water" yellow LED on LED array 96 is lit to warn the operator that more water or fluid is required. The process thereafter returns to the beginning of the loop to once again wait for interrupts or any sign that the status of the device is acceptable.

Other tests are continuously being performed on the device. For example, after the minimum fluid level test at step 218 is performed, if it is determined that reservoir 8 does have the minimum fluid level at step 18, the process proceeds to step 222 to determine whether the fluid level at reservoir 8 has reached the maximum fluid level. If it has not, a yellow LED is lit at LED array 96 to indicate to the user that the water level is low, per step 224. In this instance, the device remains operational, as the process proceeds to step 214 to determine the operational status of pump 14 and heater 18.

Other tests after the status of the device has been deemed not to be okay include: testing the connection of the fluid exchange conduit with the connector assembly per step 226, testing the temperature per step 228, testing the operation of pump 14 per step 230, testing thermostat 82 per step 232, testing thermistors 22 and 24 per step 234, testing the A/D and D/A converters per step 231, testing of data integrity per step 233 and testing for kinks in the conduit per step 235. If each of those tests shows that the status of the device is acceptable, the process proceeds to step 214 for determining whether pump 14 and heater 18 are each turned on. However, if any one of tests 226–235 fails, pump 14 and heater 18 each are turned off, as indicated per each of steps 236–244. Also, the appropriate LED at LED array 96 is lit for whichever test has failed at each of steps 236–244. The process of FIG. 5 continues until either the time for the device to remain operational has run out or until the off button is pushed, per steps 202 and 206, respectively.

With respect to tests 218 to 235, note in particular the following. Test 234 of the thermistors proceeds with the reading of the first thermistor 22. The temperature of the second thermistor 24 is then read. The respective temperatures of the thermistors are then compared. If both temperatures are the same, the power to heater 18 is turned on. On the other hand, if the respective temperatures of the thermistors are not the same, the system status fail flag for the thermistors is raised to activate a yellow LED to warn the user that a problem exists per step 244. At the same time, a "Fail Self Test" message is displayed to the user.

Another test that may require some clarification is the A/D and D/A test 231. This test involves the periodic cross checking of the analog to digital converter with the digital to analog converter to insure the integrity of the respective converters for signal conversion.

Yet another test that is worth discussing is the data integrity test 233. There all critical data including the exemplar set point 41.9° C. is read by using two independent routines. A comparison test is then performed on the data. If the comparison test fails, then the yellow LED is turned on, the message "Failed Self-Test" displayed and the appropriate alarm sequence is generated by buzzer 66. Moreover, pump 14 and heater 18 are each turned off.

Figure 6:
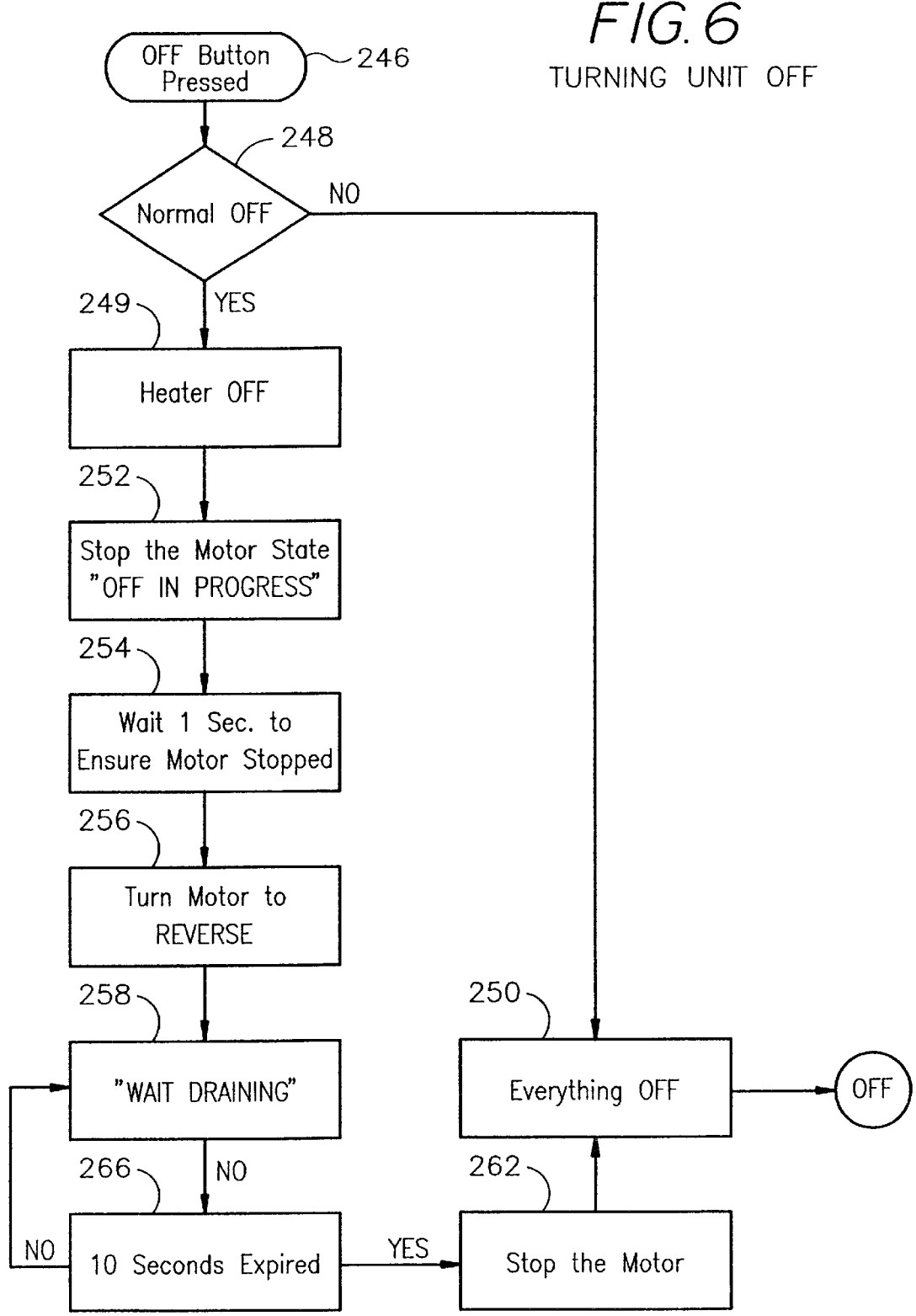
FIG. 6 is a flow chart illustrating the Turning Off process of the instant invention device.

FIG. 6 illustrates the process of the instant invention when the off button is pressed. Starting with step 246 which indicates that the off button is pressed, the process proceeds to a determination, per step 248, on whether the turning off is a "normal" off. If it is not, every component in the system is turned off per step 250, as the system is programed to assume that something catastrophic may have happened. Conversely, if the system determines that it is a "normal" off, the process proceeds to step 249 to turn off heater 18, and then step 252 to turn off the motor for pump 14. Next, per step 254, the system waits a predetermined time period, for example 1 second, to make sure that the motor for pump 14 has stopped.

Thereafter, per step 256, pump 14 is turned on in reverse, so as to reverse the circulation movement of the fluid in the system including the fluid conduit connected to the connector assembly. This is signified per step 258 whereby the fluid in both tubing 20 and the disposable fluid conduit 40 is pumped back to reservoir 8. The reverse circulation process continues for a given time period, such as for example 10 seconds, as indicated per step 266. At which time disposable fluid conduit 40 may be removed from the connector assembly, as pump 14 stops operation per step 262. A "Remove Disposable" message may also be displayed to the user. A time delay such as for example 15 second may be programmed into the system to ensure that the various components are turned off in an orderly fashion. After that, the device shuts down per step 250.

Figure 9:
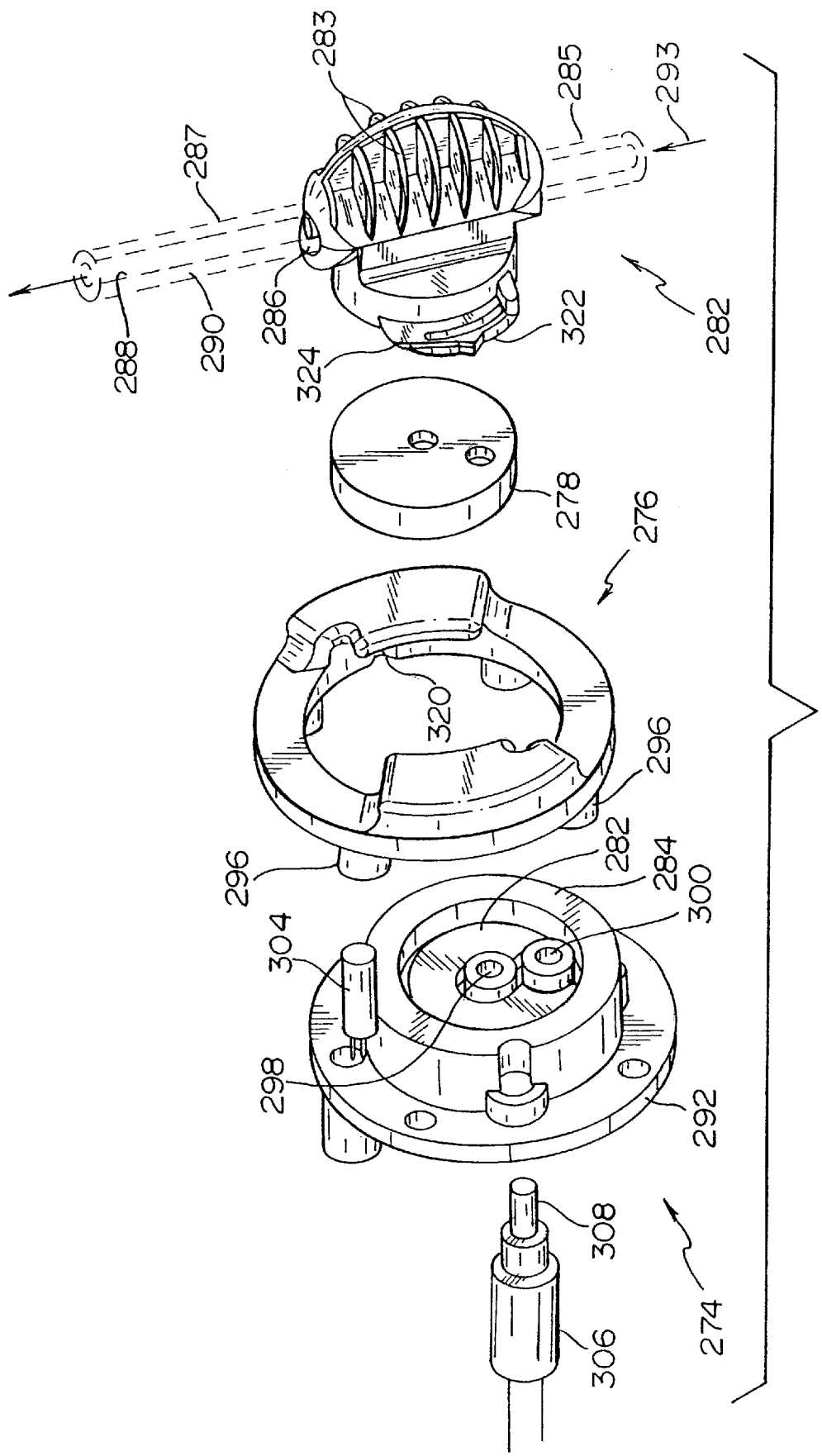
FIG. 9 is an enlarged view of the components that make up the connector assembly of the instant invention.

The connector assembly of the instant invention, as it relates to the device of the instant invention, is best shown in the perspective views of FIGS. 7, 8 and 9. As illustrated, connector assembly 270 is mounted to housing 272 of the device of the instant invention.

There are a number of components that make up the connector assembly. These include a back plate 274 which is mounted to the back of wall 272a of housing 272. Back plate 274 is secured to a housing plate 276 positioned to the exterior of wall 272a. Thus, back plate 274 and housing plate 276 are secured to each other at opposite sides of opening 280 at wall 272a as housing plate 276 superposes over back plate 274. A sealing gasket 278 is also part of the connector assembly, as it sealingly fits within an opening 280 at back plate 274 encircled by a circumferential wall 284 extending away from a flange 292 of back plate 274.

The connector for the disposable fluid conduit is shown in FIGS. 7–9 as component 282, or otherwise referred to in the instant invention as a reflux connector. As best shown in FIG. 9 per the dotted lines, a disposal or fluid conduit 287 is connected to an opening 286 of reflux connector 282. Fluid conduit 287, as is disclosed in the above incorporated by reference '898 patent, is a plastic tubing that has an inner flexible plastic tube 288 surrounded concentrically by an outer flexible plastic tube 290. The infusate to be provided to the patient is input to tube 288 per arrow 293 via another conduit or tubing 285 at another opening of reflux connector 282. The infusate, as it is being supplied to the patient, is warmed by the temperature regulated fluid that flows through tube 290.

Figure 10B:
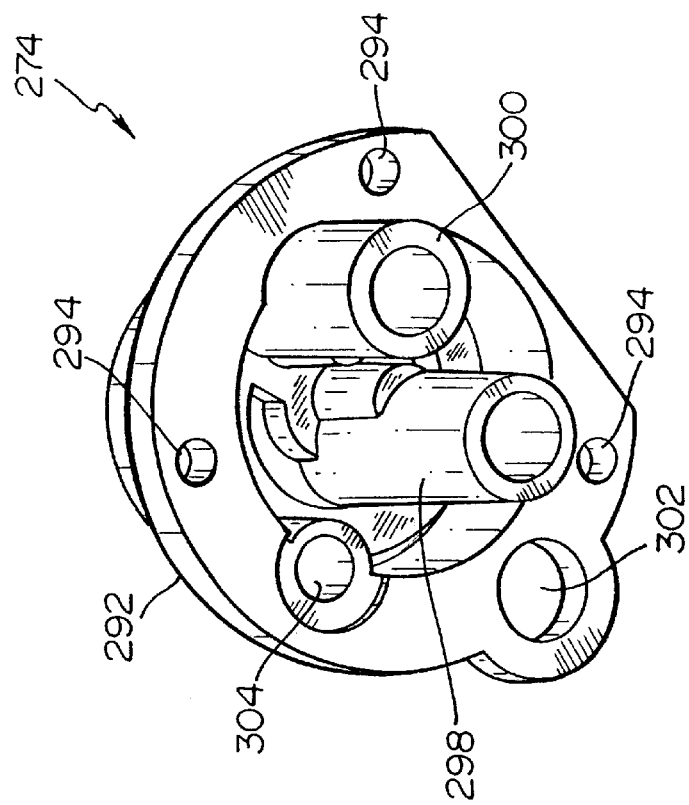
Figure 10A:
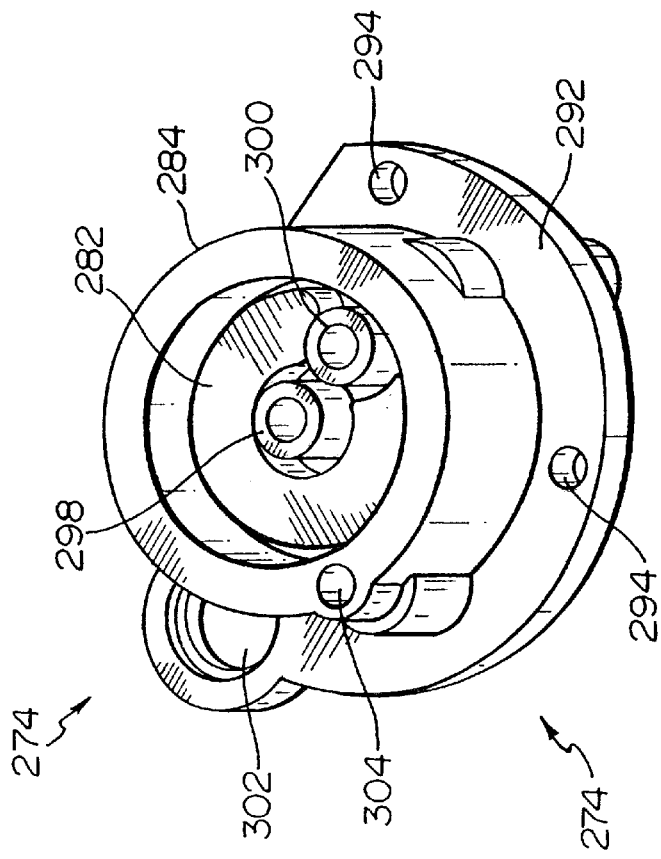
FIG. 10a is a perspective view of the support plate of the connector assembly of the instant invention which is mounted to the back of an opening of the housing to which bi-directional receptacle ports are located.

As best shown in FIGS. 10a and 10b, back plate 274 of the connector assembly of the instant invention is a one-piece molded plastic member mounted to the inside of wall 272a of housing 272 via flange. This is done by aligning a plurality of holes 294, provided along flange 292 of back plate 274, with a corresponding number of internally threaded supports 296 extending from the back of housing plate 276. See FIGS. 11a–11c. By aligning the proper support 296 with the appropriate hole 294, housing plate 276 superposes over back plate 294 at hole 280 of housing 272. A plurality of screws or other fastening means, not shown, tighten housing plate 276 to back plate 274, while at the same time anchor both back plate 274 and housing plate 276 to wall 272a of housing 272 of the device of the instant invention.

Note that the various components of the connector assembly shown in FIGS. 7–9 may be cosmetically somewhat different from those shown in FIGS. 10, 11, 12, 13 and 14. This is because the components shown in FIGS. 7–9, even though they are functionally the same as those shown in the later figures, in fact represent a different embodiment of the connector assembly. For example, connector 282 as shown in FIGS. 7–9 has at its top portion a number of fins 283 which are not germane to the inventiveness of the instant invention and accordingly are not shown in the connector 282 as illustrated in FIGS. 12 and 13.

With more particular focus to backplate 274 as shown in FIGS. 9, 10a and 10b, note that within opening 282 surrounded by circumferential wall 284 there are provided inlet/outlet ports 298 and 300. Ports 298 and 300 are the supply and return (or reflux) conduits that could be considered as part of the water circulation port 38 shown in FIG. 1. Thus, by way of supply port 298, the temperature regulated fluid, be it water or otherwise, is fed to fluid conduit 287, and specifically the outer tube 290 that surrounds inner tube 288, for warming the infusate that flows through inner tube 288. Return port 300 provides a path whereby the fluid being used to temperature regulate the infusate is circulated back to heater/cooler 18 for more heating and/or cooling, so that the fluid that is used for maintaining a desired temperature for the infusate that flows through inner tube 288 is in turn maintained at a preset temperature.

Back plate 274 is further shown to include a bore 302 through which a proximity sensor 304 is matingly fitted. Sensor 304 could be considered the same as Bio-Test sensor 42 for determining whether or not the Temp Check calibration device 46 has been mated to housing plate 276. Proximity switch 304 is an electromagnetic switch that is activated when Temp Check connector 46, which is shaped similar to reflux connector 282, is properly mated to housing plate 276. A magnet embedded in the Temp Check connector 46 activates the proximity switch 304 to inform processor 26 that a test sequence for determining the integrity of the various components of the device of the instant invention is about to take place.

Back plate 274 moreover is shown to have another bore 305 through which a position switch 307, which is the same as disposable sensor 44 shown in FIG. 1, extends. Switch 307 is a conventional switch that includes a plunger 308, which, when reflux connector 28 is mated with housing plate 26 and correctly positioned therein, is forced down into the body of switch 206 to thereby signify to processor 26 that connector 282 is correctly positioned.

Figure 11A:
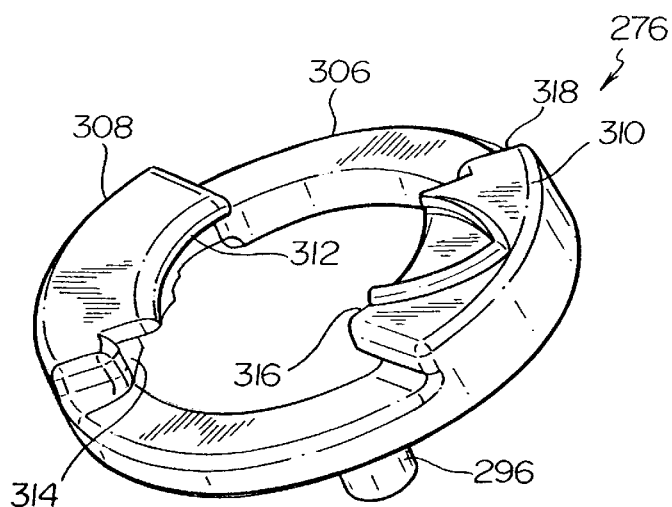
FIGS. 11a to 11c are respective perspective views of the housing plate of the connector assembly of the instant invention.
Figure 11B:
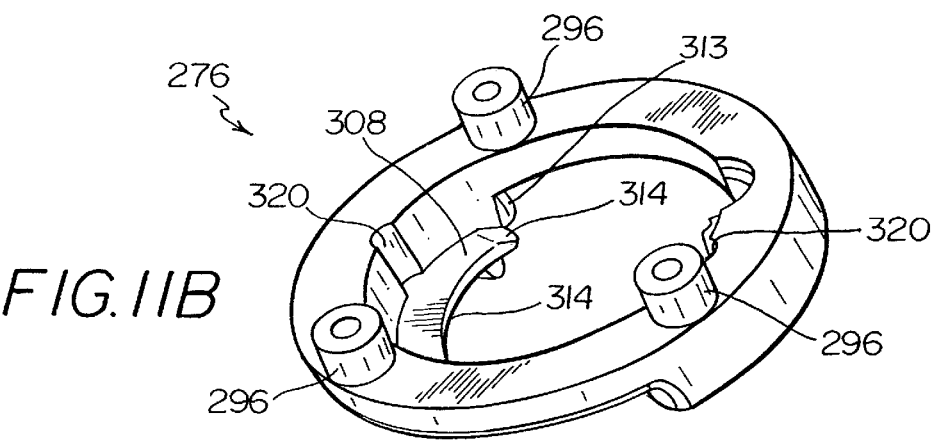
Figure 11C:
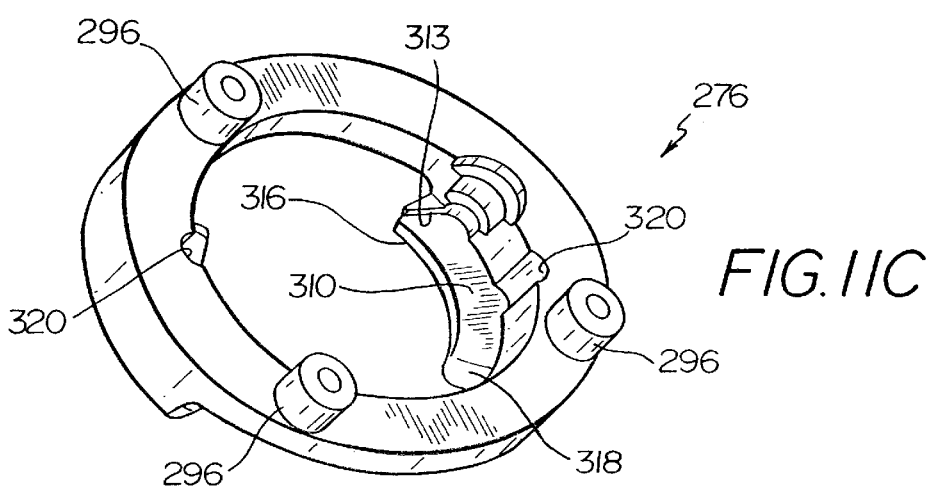

With reference to FIGS. 11a–11c, housing plate 276 is shown with greater particularity. As illustrated, housing plate 276 has a main ring-shaped body 306 that has extending therefrom two oppositely located raised portions 308 and 310. Portion 308 has an extending lip 312 and a lead in guide slot or groove 314. Portion 310 likewise has an extending lip 316 with a lead in guide slot or groove 318. In the inner circumference of body 306, there is at least one indent 320 for accepting an extension 322 at a corresponding wing 324 of reflux connector 282. See FIGS. 12 and 13. A stop 313 is provided at the end of each of grooves 314 and 318 to prevent further rotation of the base of reflux connector 282 with respect to housing plate 276.

Figure 14:
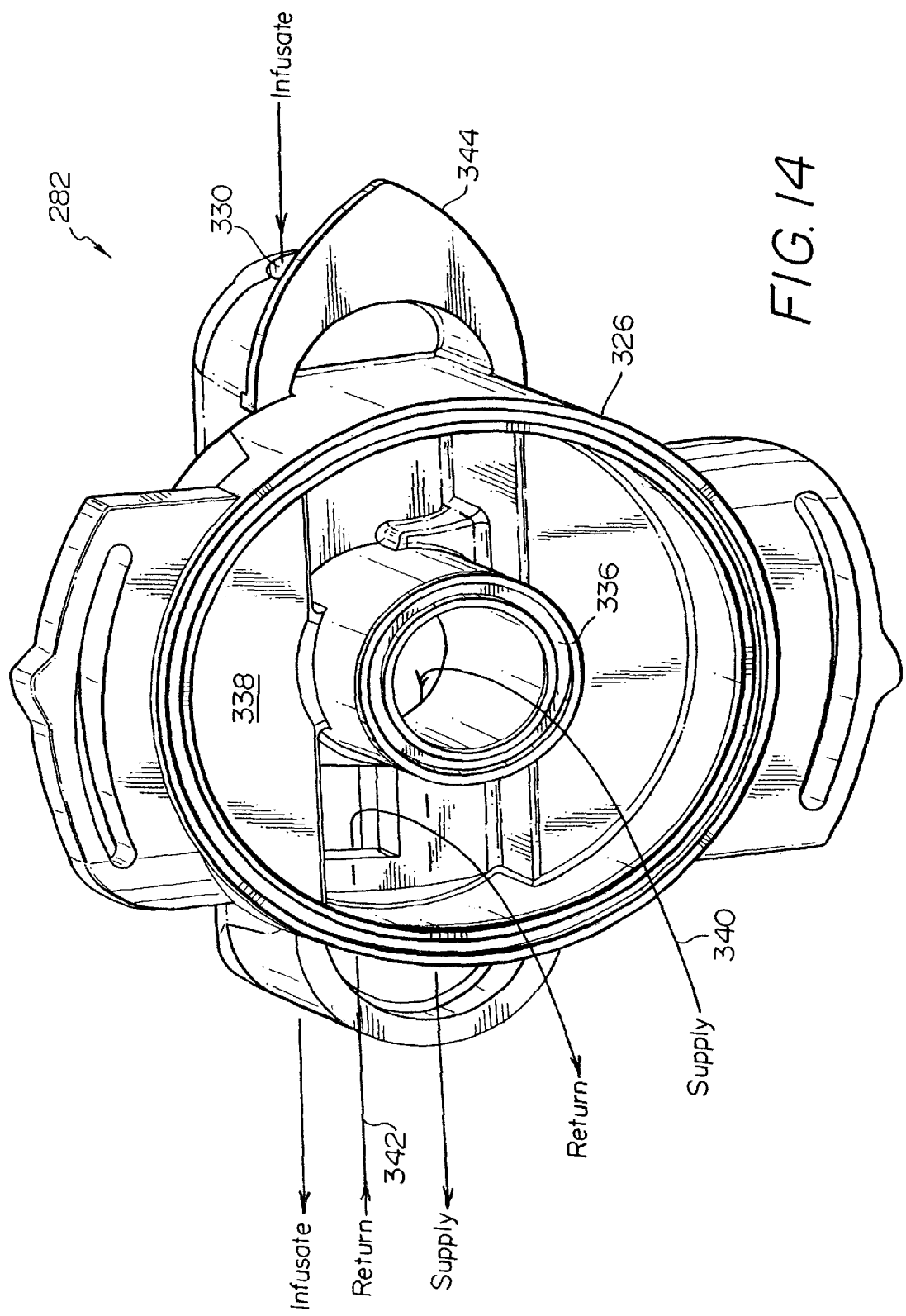
FIG. 14 is a perspective bottom view of the connector body of FIG. 12 showing the routes through which the fluid is circulated in the connector body.

Reflux connector 282, as best shown in FIGS. 12, 13 and 14, has a base 326 that is substantially ring-shaped so as to be matable with housing plate 276. An upright portion 328 extends from base 326. Extending coplanarly from base 326 are wings 322a and 322b which are mated with portions 308 and 310 of housing plate 276, respectively. To be more specific, once reflux connector 282 is positioned or superposed over plate 276 with base 326 of connector 282 being in contact with body 306 of housing plate 276, by holding and then turning or rotating raised portion 328 of connector 282 coplanarly with respect to housing plate 276, wing 324a is led by means of guide groove 318 into raised portions 310 while wing 324b is led into raised portion 308 by means of guide groove 314. With wings 322a and 322b coming into contact and snugly fitting into their corresponding detents 320, a feedback is provided to the user via his or her fingers that indeed connector 282 is positioned correctly to housing plate 276. For additional feedback, a spear shaped arm 344 extending from base 326 provides a visual indication to the user that connector 282 is positioned properly with respect to housing plate 276.

With connector 282 positioned properly with respect to housing plate 276, plunger 308 of switch 306 is pushed downwards to thereby generate a signal to processor 26 to inform the processor that indeed connector 282 has been fitted correctly to the connector assembly. If per chance base 326 of reflux connector 282 is not seated properly with respect to housing plate 276, an appropriate LED is lit at LED array 96 to inform the user that connector 282 has not been properly positioned onto the connector assembly, and the temperature regulation portion of the invention device accordingly will not be energized. See FIGS. 15a and 15b for cross-sectional views illustrating the relationship of switch 306, the connector assembly and the reflux connector 282. As mentioned previously, Temp Check calibration device 46 is shaped the same as connector 282 with the exception that a magnet is embedded therein for activating proximity switch 304, when it is mated to housing plate 276.

Further with respect to FIGS. 12, 13 and 14, note that connector 282 has a first opening 330 to which a fluid conduit such as for example 285 is fitted. Another fluid conduit such as for example 287 is fitted to an opening 332, which is located at the opposite side of upright portion 328. It is at opening 332 that the temperature regulated fluid flows for warming or cooling the infusate flowing through inner tube 288, which is connected to port 334.

FIG. 14 illustrates in greater detail the respective flows of the infusate and the temperature regulating fluid to/from the fluid conduit via reflux connector 282. In particular, note that the bottom of base 326 has a center tubular port 336, which is aligned to and mated with supply port 298 when reflux connector 282 is properly mated to housing plate 276. The space defined between base 326 and central port 336 is an open space 338 that becomes fluidly connected to return port 300 when reflux connector 282 is properly positioned with respect to housing plate 276. Accordingly, with respect to reflux connector 282, the infusate is fed to the patient via opening 330 and then tube 288 as shown in FIG. 9. The supply fluid as indicated by supply line 340 is input from supply port 298 of back plate 274 to central port 336 of reflux connector 282 and then fed to outer tube 290 for warming or cooling the infusate. And the fluid is returned to heater/cooler 18 via return path 342 through space 338 to return port 30 of back plate 274.

In essence, to properly mate reflux connector 282 to housing plate 276, base 326 of reflux connector 282 has to be rotated coplanarly with respect to body 306 of housing plate 276, or flange 292 of back plate 274, until central port 336 of connector 282 is intimately aligned with supply port 298 of back plate 274 and opening 338 of connector 282 is in an unimpeded fluid communication path with return port 300. Gasket 278 of course provides the required sealing between-port 336 and opening 338 of reflux connector 282 and supply port 298 and return port 300 of back plate 274, so that a closed loop fluid path between fluid conduit 284, at least with respect to outer tube 290 thereof, and the temperature regulating device of the instant invention is established. Ring gaskets, not shown, may also be provided between housing plate 276 and back plate 274, and between housing plate 276 and reflux connector 282, to prevent any leakage of fluid from the fluid path to the external environment.

Note further that return port 300 of back plate 274, once plate 274 is mounted to wall 272 of the housing of the device, is extended to an opening 301 (see FIGS. 7 and 8) which in turn is connected to an extension port 303 mounted on top of a shroud 304, by means of a tubing, not shown. Extension port 303 is the return port to reservoir 8, which is covered by shroud 304.

When Temp Check calibration connector 46 is mated to housing plate 276 and is sensed by Bio-Test sensor 42, i.e., proximity sensor 304, a signal is provided to processor 26 to inform the system that self testing is to take place. With reference to the flow chart shown in FIG. 16, the self test, or bio-test, begins with step 346. With Temp Check 46 in place, the system waits for the activation of either on switch 104 per step 348, or off switch 106 per step 350. Once either on switch 104 or off switch 106 is pressed, the process proceeds to determine the level of testing to be done. A number of tests are then performed as shown in the flow chart of FIG. 16.

Figure 17:
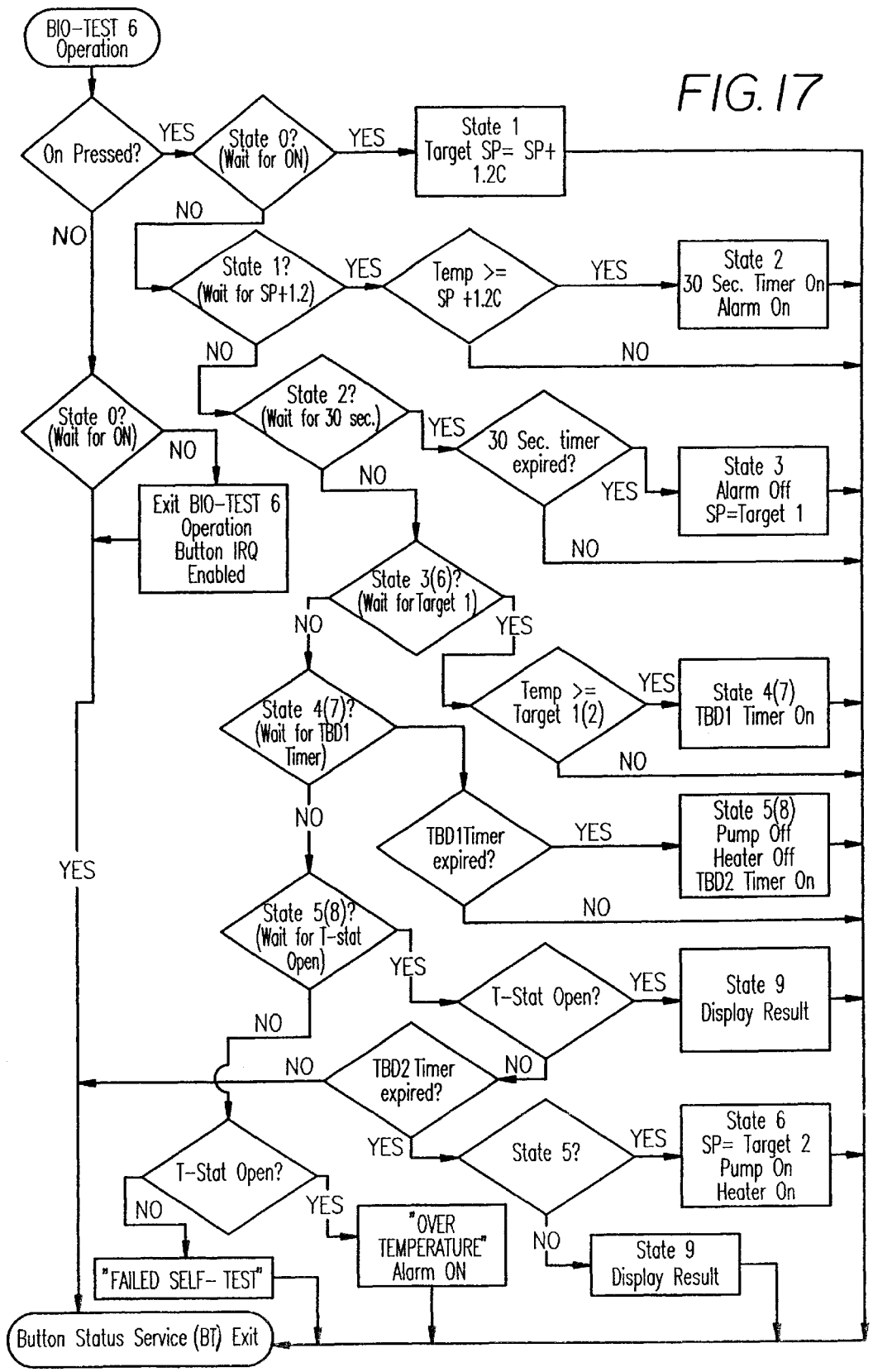
FIG. 17 is a flow chart illustrating the operation of the Bio-Test that takes place when a calibration connector device is mated to the connector assembly of the instant invention.

FIG. 17 is an illustration of the operation to be performed by the system to test the integrity of the various components. Again, it is based on Temp Check 46 being correctly mated to the connector assembly and thereafter the activation of the system by means of pressing on switch 104. The various states, from 0–9, relating to the self-testing operation are illustrated in the flow chart of FIG. 17.

Note that Temp Check connector 46 is structurally very similar to reflux connector 282 with the major differences being that no fluid conduits are connected thereto so that the fluid is refluxed directly in the Temp Check connector itself, and the embedding therein of a magnet for activating the bio-test sensor 42 when it is properly seated onto housing plate 276.

Inasmuch as the present invention is subject to many variations, modifications and changes in detail, it is intended that all matters described throughout this specification and shown in the accompanying drawings be interpreted as illustrative only and not in a limiting sense. For example, the connector assembly as discussed above could be integrated to any temperature regulating device that has a heater or cooler for heating for cooling a fluid that is to be circulated to a fluid conduit or other types of multi-lumen tubes. In fact, the connector assembly as discussed above may be retrofitted to any of the assignee's HOTLINE fluid warmers. Accordingly, it is intended that the invention be limited only the spirit and scope of the hereto appended claims.

What is claimed is:

1. A method of establishing a fluid path between a fluid temperature regulation unit whereby the temperature of a fluid is regulated and a heat exchange conduit wherethrough the temperature regulated fluid is circulated and eventually returned to said temperature regulation unit, comprising the steps of:

mounting an interface means to a given location at a wall of said temperature regulation unit for establishing a path whereby said fluid can traverse from and to said unit;

mating a connector having attached thereto said heat exchange conduit to said interface means for establishing a closed circuit for the flow of said fluid between said temperature regulation unit and said heat exchange conduit by superposing said connector over said interface means, engaging said connector to said interface means, and rotating said connector coplanarly with said interface means to sealingly mate said connector to said interface means.

2. Method of claim 1, wherein said connector comprises a base having one and other ports, further comprising the steps of:

routing said fluid from said fluid temperature regulation unit to said heat exchange conduit via said one port; and guiding said fluid from said heat exchange conduit back to said fluid temperature regulation unit via said other port.

3. Method of claim 1, wherein said rotating step further comprises the step of rotating said connector relative to said plate until a predetermined position is reached.

4. Method of claim 1, further comprising the step of:

interposing a gasket means between said interface means and said connector to prevent said fluid from leaking out of said closed circuit.

5. Method of claim 1, further comprising the step of:

activating a switch positioned relative to said interface means for enabling said fluid temperature regulation to be energized when said connector is positioned correctly relative to said interface means.

6. Method of claim 1, further comprising the steps of:

providing a sensor means relative to said interface means; and initiating calibration and temperature tests for various components in said temperature regulation unit when said sensor means senses a temperature checking connector having been properly mated to said interface means.

7. A connector assembly for coupling a heat exchange conduit to a fluid temperature regulation unit, comprising:

means mounting to said fluid temperature regulation unit at a given location at said fluid temperature regulation unit to provide a communications path for a fluid which temperature is regulated by said unit to traverse out of and into said unit; and a connector having coupled thereto said heat exchange conduit matable with said mounting means, said connector having one port for receiving and routing said fluid from said fluid temperature regulation unit to said heat exchange conduit and an other port for returning said fluid from said heat exchange conduit to said fluid temperature regulation unit, said one and other ports being configured in said connector to complete said communications path provided by said mounting means when said connector is demountably engaged to said mounting means, said connector being sealingly mated to said mounting means at said given location when said connector is rotated to a predetermined location coplanarly with respect to said mounting means.

8. Connector assembly of claim 7, wherein said mounting means comprises a plate mounted to an outside surface of said fluid temperature regulation unit, said plate including a pair of oppositely located raised portions each with a lead in groove, an indent being formed at the inner wall of each of said grooves; and wherein said connector comprises a base having two wings each for mating with a corresponding one of said raised portions, each of said wings having an extension that fits into the indent of said corresponding one raised portion so that as said base is rotated coplanarly along the plane of said plate, each of said wings is guided into its corresponding raised portion along its lead in groove, said base being determined to be properly mated with said plate when said respective extensions of said wings are mated with the indents of their corresponding raised portions.

9. Connector assembly of claim 7, wherein said connector comprises a body and said one port comprises a tubular bore internal of said body, said other port being formed by the space internal of said body surrounding said tubular bore.

10. Connector assembly of claim 7, wherein said fluid temperature regulation unit includes a housing; and wherein said mounting means further comprises a back plate mounted to the interior surface of said housing, said back plate including a circular portion mating with a hole formed on said housing whereabout said back plate is mounted, a first conduit extending through said circular portion to provide a path for said fluid which temperature is regulated by said fluid temperature regulation unit to output from said unit and a second conduit extending through said base of said circular portion to provide a path for said fluid to be returned to said fluid temperature regulation unit; and a housing plate mounted to the exterior surface of said housing and superposingly secured to said back plate, said housing plate including a pair of oppositely located raised portions each with a lead in groove.

11. Connector assembly of claim 4, wherein said connector comprises a base having two wings each for mating with a corresponding one of said raised portions of said housing plate, each of said wings being rotatably guided into its corresponding raised portion by the rotation of said base coplanarly relative to said housing plate, said base being properly mated with said housing plate when said base can no longer be rotated relative to said housing plate.

12. Connector assembly of claim 1, further comprising:

switch means positioned relative to said mounting means for preventing said fluid temperature regulation unit from being energized when said connector is not positioned to said predetermined location relative to said mounting means.

13. Connector assembly of claim 1, further comprising:

gasket means interposed between said mounting means and said connector to prevent leaks from said ports to thereby sealingly confine said fluid to said communications path.

14. Connector assembly of claim 7, further comprising:

a second gasket means positioned at the outer circumferential periphery of said connector means for preventing said fluid from escaping outside said connector assembly.

15. Connector assembly of claim 7, further comprising:

sensor means positioned relative to said mounting means for informing said temperature regulation unit that calibration and temperature tests of various components therein are to take place.

16. Connector assembly of claim 7, wherein said temperature regulation unit comprises a heat generator unit and said fluid comprises water being heated or cooled by said unit.

17. In a system having a temperature regulation unit whereby the temperature of a fluid is regulated and a heat exchange conduit wherethrough the temperature regulated fluid is routed out of and returned to said temperature regulation unit, a connector assembly for coupling said heat exchange conduit to said temperature regulation unit, comprising:

interface means mounted to a given location at a wall of said temperature regulation unit for establishing a path whereby said fluid can traverse out of and into said unit; and a connector having attached thereto said heat exchange conduit, said connector mating with said interface means for establishing a closed circuit for the flow of said fluid between said temperature regulation unit and said heat exchange conduit, said connector having one port for receiving and routing said fluid from said fluid temperature regulation unit to said heat exchange conduit and an other port for returning said fluid from said heat exchange conduit to said fluid temperature regulation unit, said connector being sealingly mated to said interface means when said connector is rotatably positioned to a predetermined location relative to and in contact with said interface means.

18. Connector assembly of claim 17, wherein said interface means comprises a back plate mounted to the back of said wall about an opening thereat and a front plate mounted to the front of said wall about said opening, said front and back plates being coupled to each other, said back plate providing one and other passages wherethrough said fluid traverses out of and into said unit, said front plate having a pair of oppositely located raised portions each with a lead in groove, an indent being formed at the inner wall of each of said grooves; and wherein said connector comprises a base having two wings each for mating with a corresponding one of said raised portions of said front plate, each of said wings having an extension that fits into the indent of said corresponding one raised portion so that as said base is rotated relative to said front plate, each of said wings is guided into its corresponding raised portion along the lead in groove of said corresponding raised portion, said base being properly mated with said plate when said respective extensions of said wings are mated with the corresponding indents of said raised portions.

19. Connector assembly of claim 17, wherein said connector comprises a base and an upright extending from said base; and wherein said one port comprises a tubular bore internal of said base extending to the interior of said upright, and said other port comprises the space internal of said base surrounding said tubular bore and leading to the interior of said upright.

20. Connector assembly of claim 17, further comprising:

switch means positioned relative to said mounting means for preventing energization of said fluid temperature regulation unit when said connector is not positioned to said predetermined location relative to said interface means.

21. Connector assembly of claim 17, further comprising:

gasket means interposed between said interface means and said connector to maintain the flow of said fluid within said port means and to prevent leaks from said connector assembly to the environment.

\* \* \* \* \*